United States Patent
Liu et al.

(10) Patent No.: US 11,077,203 B2
(45) Date of Patent: Aug. 3, 2021

(54) ANTI-SEZ6 ANTIBODY DRUG CONJUGATES AND METHODS OF USE

(71) Applicant: ABBVIE STEMCENTRX LLC, North Chicago, IL (US)

(72) Inventors: David Liu, Pacifica, CA (US); Julia Gavrilyuk, South San Francisco, CA (US); Alexander Schammel, San Francisco, CA (US)

(73) Assignee: ABBVIE STEMCENTRX LLC, North Chicago, IL (US)

( * ) Notice: Subject to any disclaimer, the term of this patent is extended or adjusted under 35 U.S.C. 154(b) by 0 days.

(21) Appl. No.: 16/908,645

(22) Filed: Jun. 22, 2020

(65) Prior Publication Data

US 2020/0316215 A1 Oct. 8, 2020

Related U.S. Application Data

(63) Continuation of application No. PCT/US2019/034701, filed on May 30, 2019.

(60) Provisional application No. 62/678,061, filed on May 30, 2018.

(51) Int. Cl.
   *A61K 47/68* (2017.01)
   *C07K 16/28* (2006.01)

(52) U.S. Cl.
   CPC ...... *A61K 47/6807* (2017.08); *A61K 47/6849* (2017.08); *A61K 47/6857* (2017.08); *C07K 16/28* (2013.01)

(58) Field of Classification Search
   CPC .......................... C07K 16/28; C07K 2317/51; A61K 47/6849; A61K 47/6857; A61K 47/6807
   See application file for complete search history.

(56) References Cited

FOREIGN PATENT DOCUMENTS

| WO | 2003092623 A2 | 11/2003 | |
|---|---|---|---|
| WO | 2005089808 A2 | 9/2005 | |
| WO | 2013126810 A1 | 8/2013 | |
| WO | 201503154 A1 | 3/2015 | |
| WO | 2015031698 A1 | 3/2015 | |
| WO | WO-2015031541 A1 * | 3/2015 | ....... G01N 33/57423 |
| WO | 2016172273 A1 | 10/2016 | |
| WO | 2017112803 A1 | 6/2017 | |
| WO | 2017214322 A1 | 12/2017 | |
| WO | WO-2017214322 A1 * | 12/2017 | ......... C07K 16/2827 |

OTHER PUBLICATIONS

Goldmacher et al (Annual Reports in Medicinal Chemistry, 2012, vol. 47, pp. 349-366) (Year: 2012).*
Shefet-Carasso and Benhar (Drug Resistance Updates, 2015, vol. 18, pp. 36-46) (Year: 2015).*
Jain et al., 2015 "Current ADC Linker Chemistry," Pharm Res 32(11):3526-40.
International Search Report from related International Application No. PCT/US2019/034701 dated Aug. 21, 2019; 7 pgs.
Written Opinion from related International Application No. PCT/US2019/034701 dated Aug. 21, 2019; 7 pgs.
International Preliminary Report on Patentability from related International Application No. PCT/US2019/034701 dated Dec. 1, 2020 (8 pages).
Goldmacher et al. (2012) "Antibody—Drug Conjugates for Targeted Cancer Therapy," Annual Reports in Medicinal Chemistry, 47:349-66.
Shefet-Carasso and Benha (2015) "Antibody-targeted drugs and drug resistance—Challenges and solutions," Drug Resistance Updates 18:36-46.

* cited by examiner

*Primary Examiner* — Karen A. Canella
(74) *Attorney, Agent, or Firm* — Dechert LLP

(57) ABSTRACT

Provided are novel anti-SEZ6 antibodies and antibody drug conjugates, and methods of using such anti-SEZ6 antibodies and antibody drug conjugates to treat cancer.

4 Claims, 6 Drawing Sheets

Figure 1:
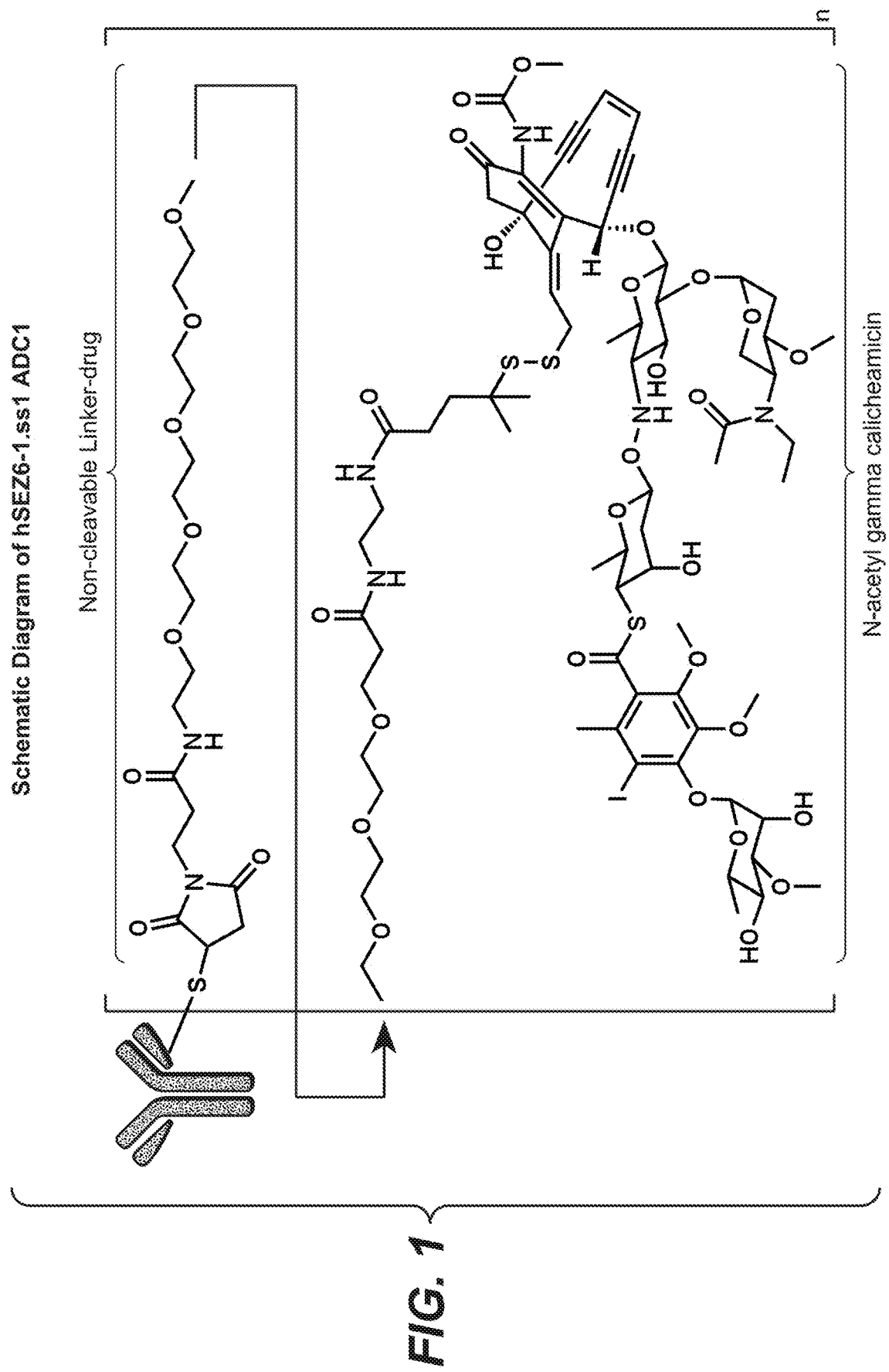

Specification includes a Sequence Listing.

ANTI-SEZ6 ANTIBODY DRUG CONJUGATES AND METHODS OF USE

1. CROSS REFERENCE TO RELATED APPLICATIONS

This application is a continuation of International Application No. PCT/US2019/034701, filed May 30, 2019, which claims the benefit under 35 U.S.C. § 119(e) of U.S. Provisional Application No. 62/678,061, filed May 30, 2018, the contents of all of which are incorporated herein in their entireties by reference thereto.

2. REFERENCE TO SEQUENCE LISTING

The instant application contains a Sequence Listing which has been submitted electronically in ASCII format and is hereby incorporated by reference in its entirety. Said ASCII copy, created on Jun. 22, 2020, is named 381493_703_US1_SL.TXT and is 29,040 bytes in size.

3. TECHNICAL BACKGROUND

The present application pertains to a novel anti-SEZ6 antibody drug conjugate, components thereof and compositions comprising the same for the treatment, diagnosis or prophylaxis of cancer and any recurrence or metastasis thereof.

4. BACKGROUND OF THE INVENTION

Differentiation and proliferation of stem cells and progenitor cells are normal ongoing processes that act in concert to support tissue growth during organogenesis, cell repair and cell replacement. The system is tightly regulated to ensure that only appropriate signals are generated based on the needs of the organism. Cell proliferation and differentiation normally occur only as necessary for the replacement of damaged or dying cells or for growth. However, disruption of these processes can be triggered by many factors including the under- or overabundance of various signaling chemicals, the presence of altered microenvironments, genetic mutations or a combination thereof. Disruption of normal cellular proliferation and/or differentiation can lead to various disorders including proliferative diseases such as cancer.

Conventional therapeutic treatments for cancer include chemotherapy, radiotherapy and immunotherapy. Often these treatments are ineffective and surgical resection may not provide a viable clinical alternative. Limitations in the current standard of care are particularly evident in those cases where patients undergo first line treatments and subsequently relapse. In such cases refractory tumors, often aggressive and incurable, frequently arise. The overall survival rates for many tumors have remained largely unchanged over the years due, at least in part, to the failure of existing therapies to prevent relapse, tumor recurrence and metastasis. There remains therefore a great need to develop more targeted and potent therapies for proliferative disorders. The current invention addresses this need.

5. SUMMARY OF THE INVENTION

In a broad aspect the present invention provides an antibody drug conjugate, or compositions thereof, which specifically binds to human SEZ6 determinants. In certain embodiments the SEZ6 determinant is a SEZ6 protein expressed on tumor cells while in other embodiments the SEZ6 determinant is expressed on tumor initiating cells. In a preferred embodiment the SEZ6 antibody drug conjugate will comprise:

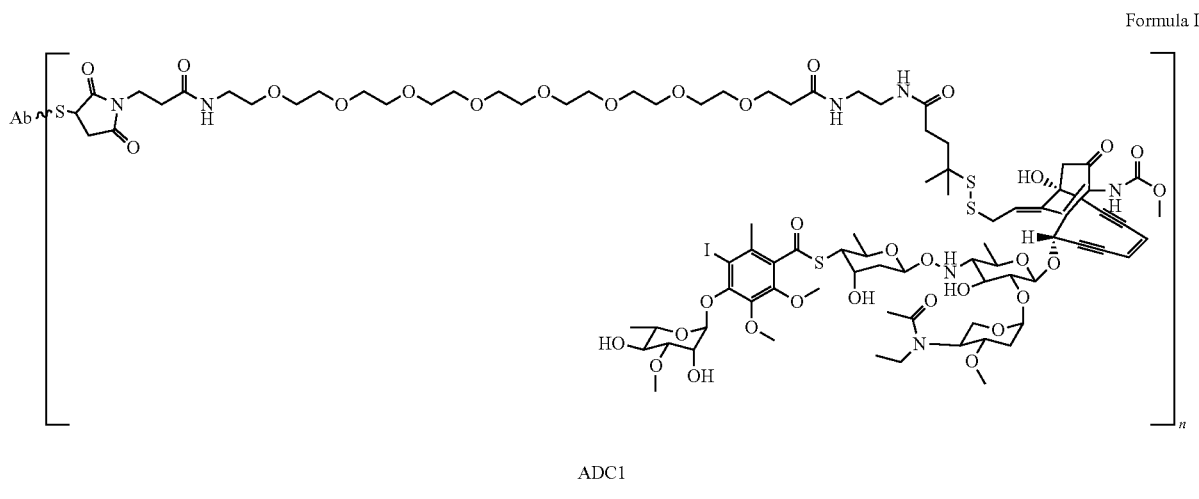

Formula I

ADC1 wherein Ab comprises an anti-SEZ6 antibody having a heavy chain of SEQ ID NO:3 and a light chain of SEQ ID NO:4 and wherein n is 2. For the purposes of the instant disclosure this antibody drug conjugate shall be termed "hSEZ6-1.ss1 ADC1" unless otherwise indicated.

In selected embodiments the present invention comprises an antibody comprising a heavy chain of SEQ ID NO:3 and a light chain of SEQ ID NO:4. In certain aspects the invention comprises a nucleic acid encoding a heavy chain (SEQ ID NO:3) or light chain (SEQ ID NO:4) of the anti-SEZ6 antibody of the invention or a fragment thereof. In other embodiments the invention comprises a vector comprising one or more of the above described nucleic acids or a host cell comprising said nucleic acids or vectors.

In yet another embodiment the invention comprises a calicheamicin drug linker, or a pharmaceutically acceptable salt or solvate thereof, comprising the structure set forth in Formula II.

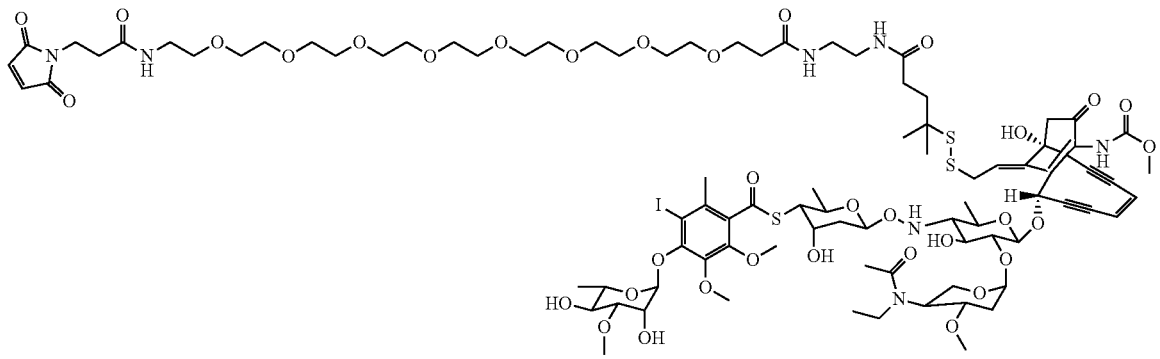

Formula II

As set forth above the present invention provides an anti-SEZ6 antibody drug conjugate wherein the antibody is conjugated to one or more non-cleavable calicheamicin payloads of Formula II. Further provided are pharmaceutical compositions comprising an anti-SEZ6 ADC as disclosed herein. In certain embodiments the compositions will comprise a selected drug-antibody ratio (DAR) where the predominant ADC species (e.g., comprising 2 calicheamicin warheads) comprises greater than about 50%, greater than about 60%, greater than about 70%, greater than about 80%, greater than about 90% or greater than about 95% of the species present. Preferably the drug loading of the predominant species will be 2.

Another aspect of the invention is a method of treating cancer comprising administering an antibody drug conjugate or a pharmaceutical composition such as those described herein to a subject in need thereof. In certain embodiments the subject will be suffering from lung cancer and, in selected embodiments, small cell lung cancer (SCLC).

In other embodiments the disclosed ADC will comprise a safety margin (derived as described herein) greater than 6. In other embodiments the safety margin will be greater than 7 and in yet other embodiments the safety margin will be greater than 8 or greater than 9. In still other embodiments the safety margin will be about 10.

In still another embodiment the invention comprises a method of reducing tumor initiating cells in a tumor cell population, wherein the method comprises contacting (e.g. in vitro or in vivo) a tumor initiating cell population with an antibody drug conjugate as described herein whereby the frequency of the tumor initiating cells is reduced.

In one aspect, the invention comprises a method of delivering a cytotoxin to a cell comprising contacting the cell with the disclosed antibody drug conjugate.

In another aspect the present invention also provides kits or devices and associated methods that are useful in the treatment of lung cancer. To this end the present invention preferably provides an article of manufacture useful for treating lung cancer comprising a receptacle containing the SEZ6 ADC and instructional materials for using the ADC to treat lung cancer (e.g., small cell lung cancer) or provide a dosing regimen for the same. In other embodiments the disclosed kits will comprise instructions, labels, inserts, readers or the like indicating that the kit or device is used for the treatment of lung cancer or provide a dosing regimen for the same.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description.

6. BRIEF DESCRIPTION OF THE FIGURES

Figure 2:
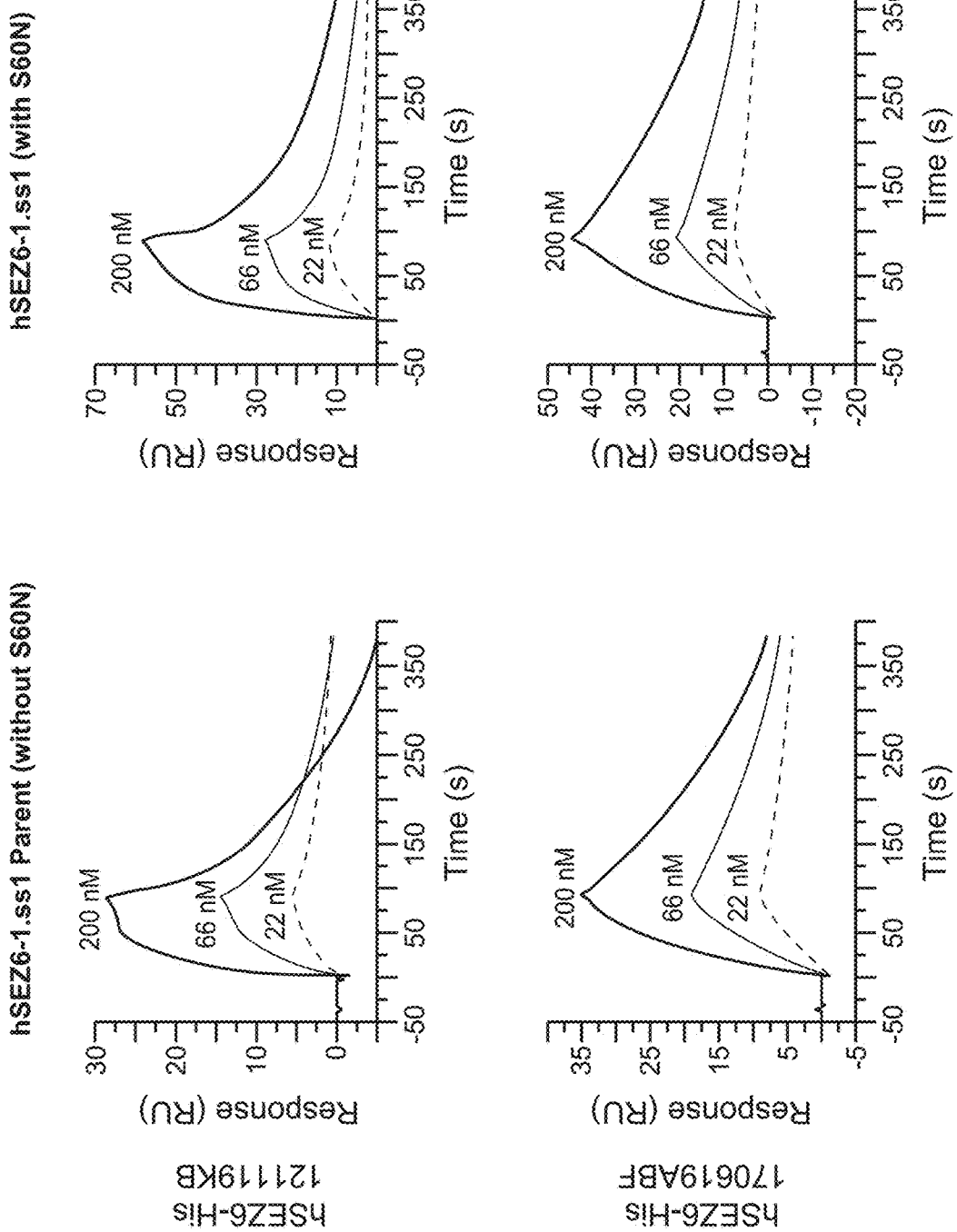
Figure 3:
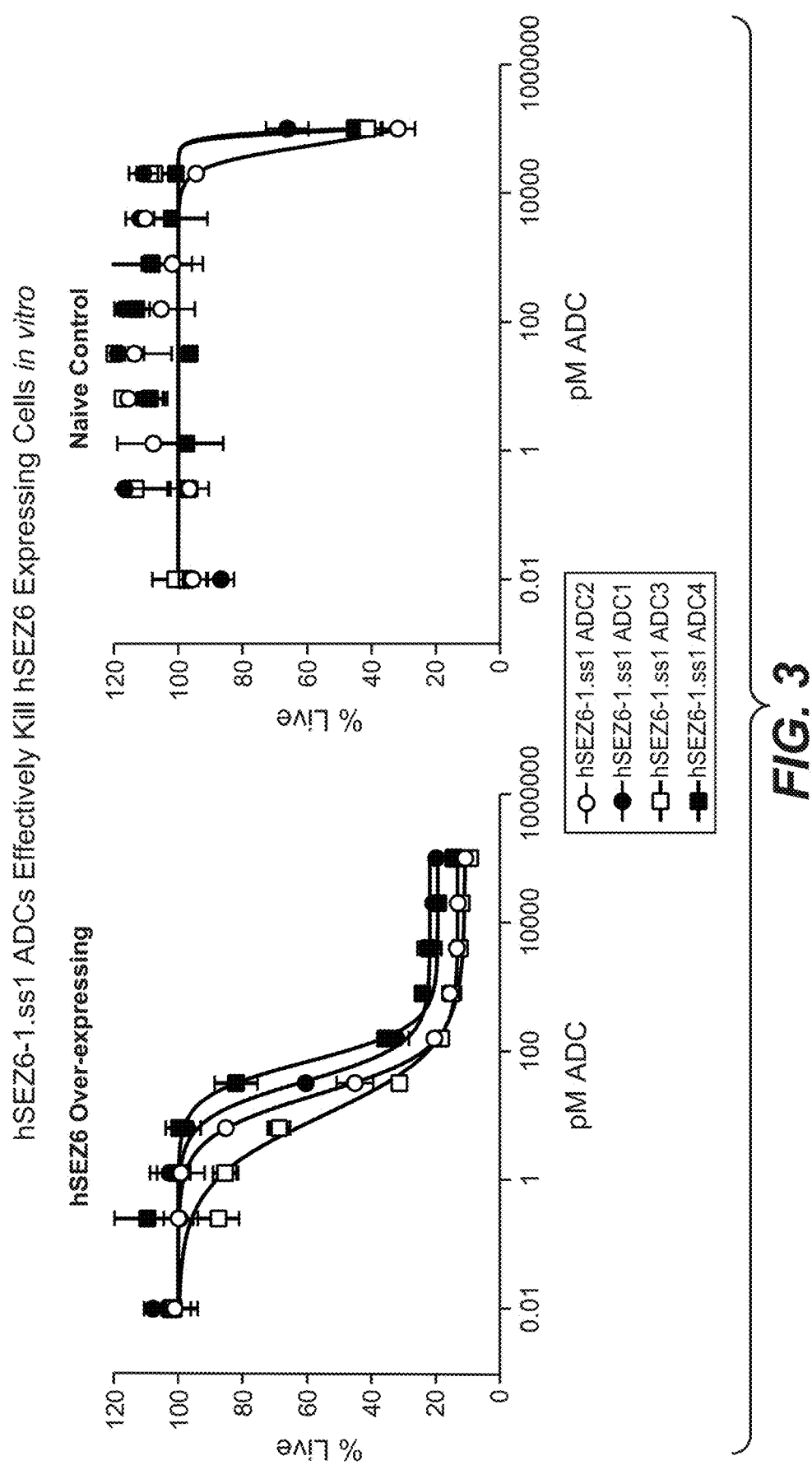
Figures 4A, 4B:
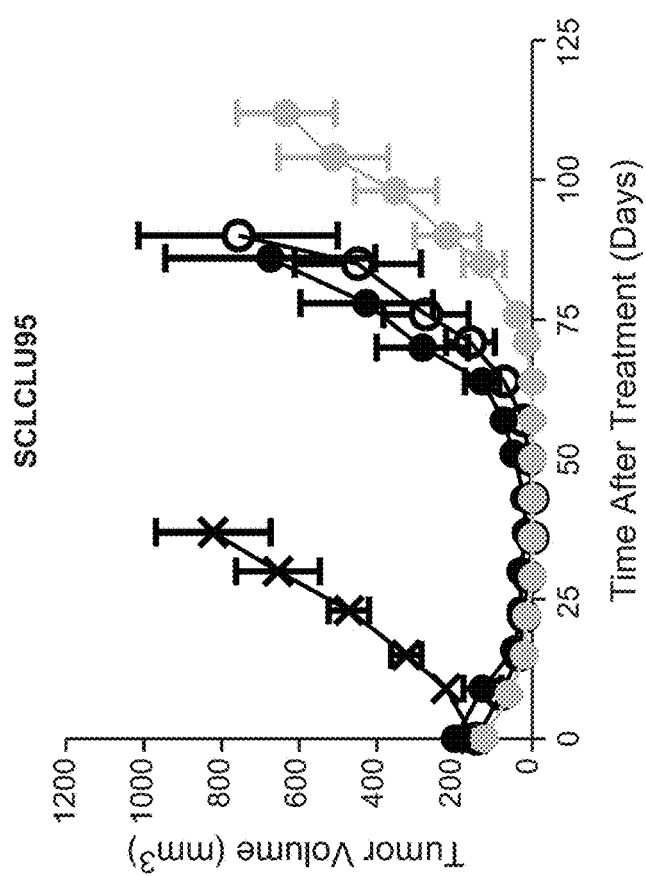
Figure 5B:
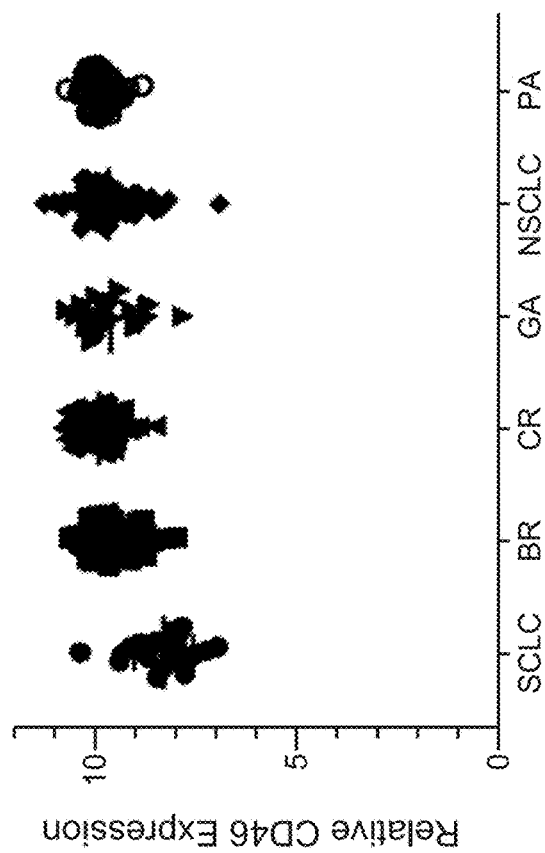
Figure 5A:
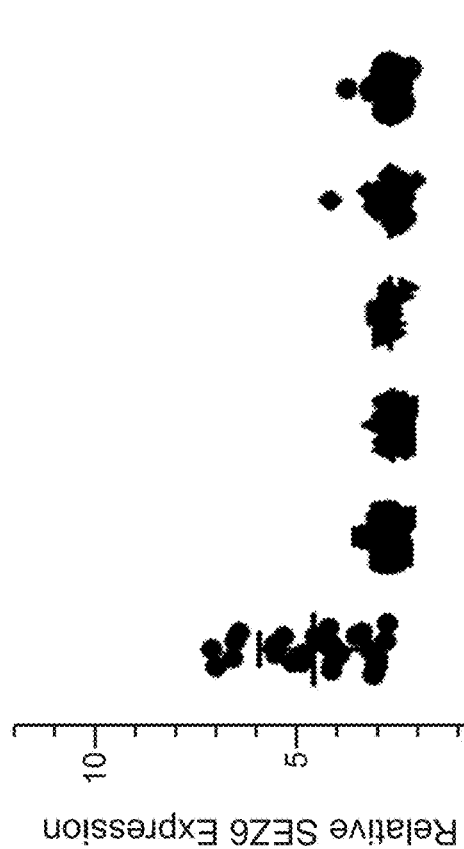
Figures 5C, 5D:
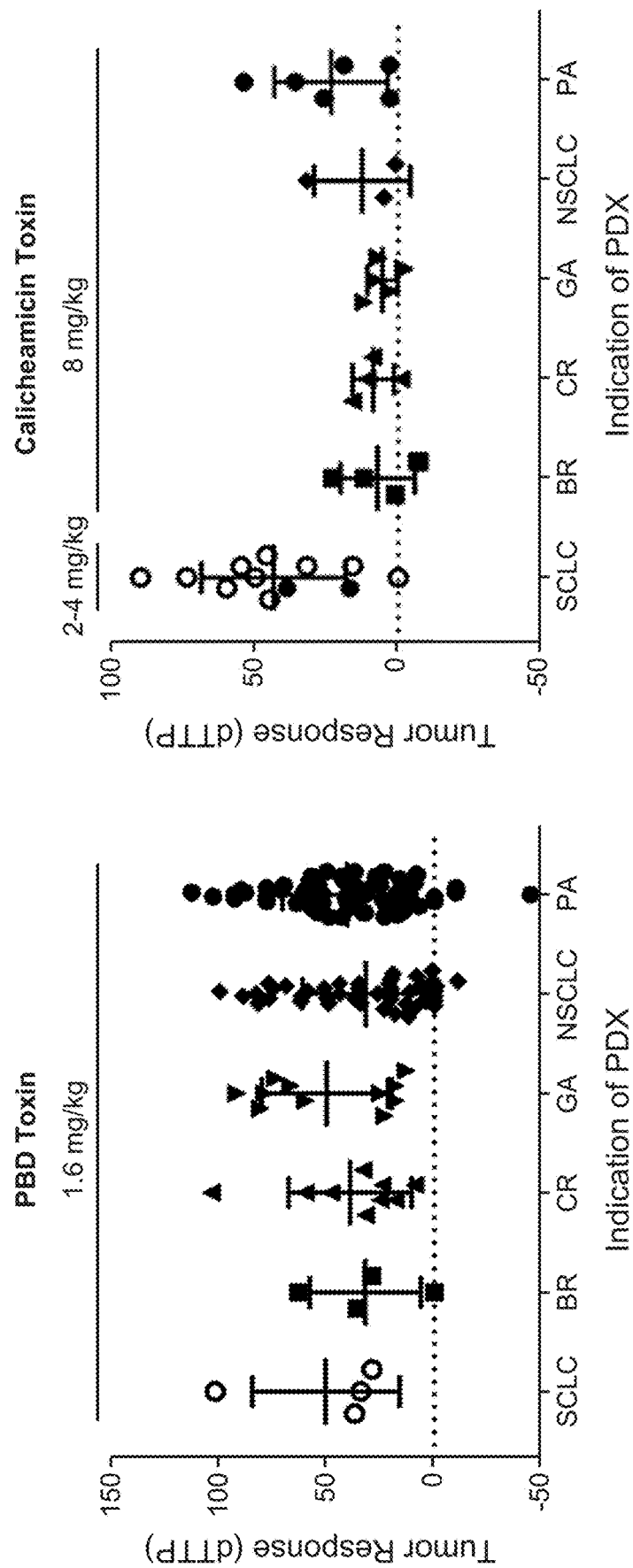

FIG. 1 is a schematic representation of hSEZ6-1.ss1 ADC1;

FIG. 2 provides binding curves demonstrating that a SEZ6 antibody comprising the S60N mutation has an affinity profile that is substantially the same as a SEZ6 antibody without the S60N mutation;

FIG. 3 demonstrates that the disclosed SEZ6 ADCs effectively kill cells expressing hSEZ6 in a dose dependent manner while not depleting naëve control cells that do not express hSEZ6;

FIGS. 4A and 4B depict the ability of the disclosed SEZ6 ADCs to retard small cell lung cancer tumor growth in immunocompromised mice implanted with the SCLC LU 95 (FIG. 4A) and SCLC LU 149 (FIG. 4B); and FIGS. 5A-5D demonstrate that SCLC tumors are particularly susceptible to treatment with ADCs comprising a non-cleavable calicheamicin linker drug wherein FIGS. 5A and 5B show, respectively, relative expression levels of SEZ6 and a positive control antigen in various tumor cell lines, FIG. 5C shows that a PBD toxin uniformly kills different type of cancer cells and FIG. 5D shows that calicheamicin is particularly active in killing SCLC cells.

7. DETAILED DESCRIPTION OF THE INVENTION

Disclosed herein are non-limiting, illustrative embodiments of the invention that exemplify the principles thereof. Any section headings used herein are for organizational purposes only and are not to be construed as limiting the subject matter described. For the purposes of the instant disclosure all identifying sequence accession numbers may be found in the NCBI Reference Sequence (RefSeq) database and/or the NCBI GenBank® archival sequence database unless otherwise noted.

The present invention provides novel anti-SEZ6 ADCs and components thereof (including the hSEZ6-1.ss1 antibody and the calicheamicin drug linker of Formula II) comprising a site-specific anti-SEZ6 antibody targeting agent and calicheamicin cytotoxic payload. As discussed in more detail below and set forth in the appended Examples, the disclosed anti-SEZ6 ADC is particularly efficacious in suppressing tumor growth when compared with other anti-SEZ6 ADCs.

The ability to effectively reduce or eliminate tumor and/or cancer stem cells through use of the SEZ6 ADC disclosed herein is due to the relative lack of off-site toxicity which allows for increased dosing. This, in turn provides for higher calicheamicin levels at the tumor site than other calicheamicin ADCs and results in increased cell killing. As shown in the appended Examples the increased toxin concentration at the tumor-site provides for extended tumor suppression in immunocompromised mice. Thus, the SEZ6 ADC disclosed herein will likely exhibit a favorable therapeutic index and may be used in the treatment and/or prevention of selected proliferative disorders such as small cell lung cancer or progression or recurrence thereof.

SEZ6 Cancer Stem Cells

It has been postulated that SCLC is bronchogenic in origin, arising in part from pulmonary neuroendocrine cells (Galluzzo and Bocchetta, 2011; PMID: 21504320). Whatever the cellular source of origin for these tumors, it is clear that they show a poorly differentiated endocrine phenotype, often are highly proliferative and aggressive, and frequently over-express neural proteins. The resultant elevation of neural expression markers in these tumors that otherwise may be primarily restricted to the nervous system or show limited expression during development, of which SEZ6 may be an exemplar, may therefore offer a unique therapeutic target for tumors with the neuroendocrine phenotype.

SEZ6 expression is associated with various tumorigenic cell subpopulations in a manner which renders them susceptible to treatment as set forth herein. In this regard the invention provides hSEZ6-1.ss1 ADC1 which may be particularly useful for targeting tumorigenic cells thereby facilitating the treatment, management and/or prevention of cancer. Whether by inhibition or elimination of the tumorigenic cells, modification of their potential (for example, by induced differentiation or niche disruption) or otherwise interfering with the ability of tumorigenic cells to influence the tumor environment or other cells, the present invention allows for more effective treatment of cancer by inhibiting tumorigenesis, tumor maintenance and/or metastasis and recurrence. It will further be appreciated that the same characteristics of the disclosed antibodies make them particularly effective at treating recurrent tumors which have proved resistant or refractory to standard treatment regimens.

Methods that can be used to assess a reduction in the frequency of tumorigenic cells include, but are not limited to, cytometric or immunohistochemical analysis, preferably by in vitro or in vivo limiting dilution analysis (Dylla et al. 2008, PMID: PMC2413402 and Hoey et al. 2009, PMID: 19664991).

The ability of the antibodies of the current invention to reduce the frequency of tumorigenic cells can therefore be determined using the techniques and markers known in the art. In some instances, the anti-SEZ6 ADCs may reduce the frequency of tumorigenic cells by 10%, 15%, 20%, 25%, 30% or even by 35%. In other embodiments, the reduction in frequency of tumorigenic cells may be in the order of 40%, 45%, 50%, 55%, 60% or 65%. In certain embodiments, the disclosed compounds may reduce the frequency of tumorigenic cells by 70%, 75%, 80%, 85%, 90% or even 95%. It will be appreciated that any reduction of the frequency of tumorigenic cells is likely to result in a corresponding reduction in the tumorigenicity, persistence, recurrence and aggressiveness of the neoplasia.

Antibody Structure

Antibodies and variants and derivatives thereof, including accepted nomenclature and numbering systems, have been extensively described, for example, in Abbas et al. (2010), *Cellular and Molecular Immunology* ($6^{th}$ Ed.), W. B. Saunders Company; or Murphey et al. (2011), *Janeway's Immunobiology* ($8^{th}$ Ed.), Garland Science.

An "antibody" or "intact antibody" typically refers to a Y-shaped tetrameric protein comprising two heavy (H) and two light (L) polypeptide chains held together by covalent disulfide bonds and non-covalent interactions. Each light chain is composed of one variable domain (VL) and one constant domain (CL). Each heavy chain comprises one variable domain (VH) and a constant region, which in the case of IgG, IgA, and IgD antibodies, comprises three domains termed CH1, CH2, and CH3 (IgM and IgE have a fourth domain, CH4). In IgG, IgA, and IgD classes the CH1 and CH2 domains are separated by a flexible hinge region, which is a proline and cysteine rich segment of variable length (from about 10 to about 60 amino acids in various IgG subclasses). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues.

As used herein the term "antibody" specifically includes humanized IgG1 monoclonal antibodies comprising kappa (κ) light chains.

The variable domains of antibodies show considerable variation in amino acid composition from one antibody to another and are primarily responsible for antigen recognition and binding. Variable regions of each light/heavy chain pair form the antibody binding site such that an intact IgG antibody has two binding sites (i.e. it is bivalent). VH and VL domains comprise three regions of extreme variability, which are termed hypervariable regions, or more commonly, complementarity-determining regions (CDRs), framed and separated by four less variable regions known as framework regions (FRs). Non-covalent association between the VH and the VL region forms the Fv fragment (for "fragment variable") which contains one of the two antigen-binding sites of the antibody.

As used herein, the assignment of amino acids to each domain, framework region and CDR will be in accordance with one of the schemes provided by Kabat et al. (1991) *Sequences of Proteins of Immunological Interest* ($5^{th}$ Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) *Handbook of Therapeutic Antibodies*, $3^{rd}$ Ed., Wily-VCH Verlag GmbH and Co or AbM (Oxford Molecular/MSI Pharmacopia) unless otherwise noted. As is well known in the art variable region residue numbering is typically as set forth in Chothia or Kabat. Amino acid residues which comprise CDRs as defined by Kabat, Chothia, MacCallum (also known as Contact) and AbM as obtained from the Abysis website database (infra.) are set out below in Table 1. Note that MacCallum uses the Chothia numbering system.

TABLE 1

|         | Kabat  | Chothia | MacCallum | AbM    |
|---------|--------|---------|-----------|--------|
| VH CDR1 | 31-35  | 26-32   | 30-35     | 26-35  |
| VH CDR2 | 50-65  | 52-56   | 47-58     | 50-58  |
| VH CDR3 | 95-102 | 95-102  | 93-101    | 95-102 |
| VL CDR1 | 24-34  | 24-34   | 30-36     | 24-34  |
| VL CDR2 | 50-56  | 50-56   | 46-55     | 50-56  |
| VL CDR3 | 89-97  | 89-97   | 89-96     | 89-97  |

Variable regions and CDRs in an antibody sequence can be identified according to general rules that have been developed in the art (e.g., as set forth above) or by aligning the sequences against a database of known variable regions. Methods for identifying these regions are described in Kontermann and Dubel, eds., Antibody Engineering, Springer, New York, N.Y., 2001 and Dinarello et al., Current Protocols in Immunology, John Wiley and Sons Inc., Hoboken, N.J., 2000. Exemplary databases of antibody sequences are described in, and can be accessed through, the "Abysis" website at www.bioinf.org.uk/abs (maintained by A. C. Martin in the Department of Biochemistry & Molecular Biology University College London, London, England) and the VBASE2 website at www.vbase2.org, as described in Retter et al., Nucl. Acids Res., 33 (Database issue): D671-D674 (2005).

Preferably sequences are analyzed using the Abysis database, which integrates sequence data from Kabat, IMGT and the Protein Data Bank (PDB) with structural data from the PDB. See Dr. Andrew C. R. Martin's book chapter *Protein Sequence and Structure Analysis of Antibody Variable Domains.* In: *Antibody Engineering Lab Manual* (Ed.: Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein. Unless otherwise indicated, all CDRs set forth herein are derived according to the Abysis database website as per Kabat et al.

For heavy chain constant region amino acid positions discussed in the invention, numbering is according to the Eu index first described in Edelman et al., 1969, Proc. Natl. Acad. Sci. USA 63(1): 78-85 describing the amino acid sequence of the myeloma protein Eu, which reportedly was the first human IgG1 sequenced. The Eu index of Edelman is also set forth in Kabat et al., 1991 (supra.). Thus, the terms "Eu index as set forth in Kabat" or "Eu index of Kabat" or "Eu index" or "Eu numbering" in the context of the heavy chain refers to the residue numbering system based on the human IgG1 Eu antibody of Edelman et al. as set forth in Kabat et al., 1991 (supra.) The numbering system used for the light chain constant region amino acid sequence is similarly set forth in Kabat et al., (supra.).

Those of skill in the art will appreciate that the heavy and light chain constant region sequences of the hSEZ6-1.ss1 antibody have been engineered as disclosed herein to provide unpaired cysteines. These constant regions are then operably associated with the disclosed heavy and light chain variable regions using standard molecular biology techniques to provide the full-length antibody chains that are incorporated in the disclosed hSEZ6-1.ss1.

Antibody Generation and Production

The humanized antibody hSEZ6-1.ss1 is produced as set forth in Examples 1 and 2 appended hereto and the resulting amino acid sequences of the full length heavy chain and full length light chain are set forth immediately below as SEQ ID NO:3 and SEQ ID NO:4. As discussed below the heavy chain of the humanized antibody comprises a S60N mutation designed to inactivate a glycosylation site and a C220S mutation (numbered according to the EU index of Kabat) that provides the free cysteine on the light chain. Note that in the heavy chain the S60N and the C220S mutations are underlined while the resulting free cysteine at position 214 is underlined in the light chain. The variable region of both chains is depicted in bold type.

(SEQ ID NO: 3)
EVQLVQSGAEVKKPGESLKISCKGSGYSFTSSWINWVRQMPGKGLEWMGR

IYPGEGDTNYNGNFEGQVTISADKSISTAYLQWSSLKASDTAMYYCTRGL

VMDYWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSSDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG (SEQ ID NO: 4)
EIVLTQSPATLSLSPGERATLSCRASQSVDYNGISYMHYVYQQKPGQAPR

LLIYAASNVQSGIPARFSGSGSGTDFTLTISSLEPEDFAVYYCQQSIEDP

PTFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

In addition, compatible nucleic acid sequences encoding the aforementioned full length heavy and light chains are set forth immediately below as SEQ ID NO:5 and SEQ ID NO:6 respectively.

HEAVY CHAIN NUCLEIC ACID SEQUENCE (with introns)
(SEQ ID NO: 5)
gaagtccaactcgtccaatccggtgccgaagtgaaaaagcctggggaatc cctgaagatcagctgcaagggatccggttactcgttcacctcctcctgga ttaactgggtccggcagatgcccggaaagggactggagtggatgggcaga atctatccgggcgaaggggacactaattacaacggaaacttcgagggcca ggtcaccatttcggccgataagagcatctcaaccgcgtacttgcagtggt caagcctgaaggcttccgacaccgccatgtactactgtactcgcggcctt gtgatggactactggggacagggaactctcgtgaccgtgtcgtccgcctc taccaagggccttccgtgttccctctggccccctcgagcaagagcacct ctggggcacagcggccctgggctgcctggtcaaggactacttccccgag ccggtgacggtgtcgtggaactcaggcgccctgaccagcggcgtgcacac cttcccggctgtcctacagtcctcaggactctactccctcagcagcgtgg tgaccgtgcctccagcagcttgggcacccagacctacatctgcaacgtg aatcacaagcccagcaacaccaaggtggacaagaaagttggtgagaggcc agcacagggagggagggtgtctgctggaagccaggctcagcgctcctgcc tggacgcatcccggctatgcagccccagtccagggcagcaaggcaggccc -continued

```
cgtctgcctcttcacccggaggcctctgcccgccccactcatgctcaggg agagggtcttctggcttttccccaggctctgggcaggcacaggctaggt gccctaacccaggccctgcacacaaaggggcaggtgctgggctcagacc tgccaagagccatatccgggaggaccctgccctgacctaagcccacccc aaaggccaaactctccactccctcagctcggacaccttctctcctcccag attccagtaactcccaatcttctctctgcagagcccaaatctagtgacaa aactcacacatgccaccgtgcccaggtaagccagcccaggcctcgccct ccagctcaaggcgggacaggtgccctagagtagcctgcatccagggacag gccccagccgggtgctgacacgtccacctccatctcttcctcagcacctg aactcctgggggaccgtcagtcttcctcttcccccaaaacccaaggac accctcatgatctcccggacccctgaggtcacatgcgtggtggtggacgt gagccacgaagaccctgaggtcaagttcaactggtacgtggacggcgtgg aggtgcataatgccaagacaaagccgcgggaggagcagtacaacagcacg taccgtgtggtcagcgtcctcaccgtcctgcaccaggactggctgaatgg caaggagtacaagtgcaaggtctccaacaaagccctcccagcccccatcg agaaaccatctccaaagccaaaggtgggacccgtggggtgcgagggcca catggacagaggccggctcggcccaccctctgccctgagagtgaccgctg taccaacctctgtccctacagggcagccccgagaaccacaggtgtacacc ctgcccccatcccgggatgagctgaccaagaaccaggtcagcctgacctg cctggtcaaaggcttctatcccagcgacatcgccgtggagtgggagagca atgggcagccggagaacaactacaagaccacgcctcccgtgctggactcc gacggctccttcttcctctacagcaagctcaccgtggacaagagcaggtg gcagcaggggaacgtcttctcatgctccgtgatgcatgaggctctgcaca accactacacgcagaagagcctctccctgtctccgggt
```

LIGHT CHAIN NUCLEIC ACID SEQUENCE
(SEQ ID NO: 6)

```
gaaatcgtgttgacccagtccccgctaccctgtcactgagcccggaga acgcgcgactctgtcctgccgggcatcccagtccgtggactacaacggaa tctcctacatgcactggtatcagcaaaagccaggccaagccccgagactg ctcatctacgccgcctcgaacgtgcagagcggtattccgcgcggttctc cggctcgggcagcggaaccgattttaccctcactatctcgtcacttgaac ctgaggacttcgccgtgtactactgccagcagtccattgaggacccgcct actttcggggggggaaccaaagtcgagatcaagcggactgtggctgcacc aagtgtcttcatcttcccgccatctgatgagcagttgaaatctggaactg cctctgttgtgtgcctgctgaataacttctatcccagagaggccaaagta cagtggaaggtggataacgccctccaatcgggtaactcccaggagagtgt cacagagcaggacagcaaggacagcacctacagcctcagcagcaccctga cgctgagcaaagcagactacgagaaacacaaagtctacgcctgcgaagtc acccatcagggcctgagctcgcccgtcacaaagagcttcaacaggggaga gtgt
```

The SEZ6 antibody component of the instant invention has been engineered to facilitate efficient conjugation of the calic rated from other cellular components or other contaminants, e.g., other cellular nucleic acids or proteins, by standard techniques, including alkaline/SDS treatment, CsCl banding, column chromatography, agarose gel electrophoresis and others well known in the art. A nucleic acid of the invention can be, for example, DNA (e.g. genomic DNA, cDNA), RNA and artificial variants thereof (e.g., peptide nucleic acids), whether single-stranded or double-stranded or RNA, RNA and may or may not contain introns. In selected embodiments the nucleic acid is a cDNA molecule.

Nucleic acids of the invention can be obtained using standard molecular biology techniques. For antibodies expressed by hybridomas (e.g., hybridomas prepared as described in the Examples below), cDNAs encoding the light and heavy chains of the antibody can be obtained by standard PCR amplification or cDNA cloning techniques. For antibodies obtained from an immunoglobulin gene library (e.g., using phage display techniques), nucleic acid molecules encoding the antibody can be recovered from the library.

DNA fragments encoding VH and VL segments can be further manipulated by standard recombinant DNA techniques, for example to convert the variable region genes to full-length antibody chain genes, to Fab fragment genes or to a scFv gene. In these manipulations, a VL- or VH-encoding DNA fragment is operably linked to another DNA fragment encoding another protein, such as an antibody constant region or a flexible linker. The term "operably linked", as used in this context, means that the two DNA fragments are joined such that the amino acid sequences encoded by the two DNA fragments remain in-frame.

The isolated DNA encoding the VH region can be converted to a full-length heavy chain gene by operably linking the VH-encoding DNA to another DNA molecule encoding heavy chain constant regions (CH1, CH2 and CH3 in the case of IgG1). The sequences of human heavy chain constant region genes are known in the art (see e.g., Kabat, et al. (1991) (supra)) and DNA fragments encompassing these regions can be obtained by standard PCR amplification.

Isolated DNA encoding the VL region can be converted to a full-length light chain gene by operably linking the VL-encoding DNA to another DNA molecule encoding the light chain constant region, CL. The sequences of human light chain constant region genes are known in the art (see e.g., Kabat, et al. (1991) (supra)) and DNA fragments encompassing these regions can be obtained by standard PCR amplification. The light chain constant region can be a kappa or lambda constant region, but most preferably is a kappa constant region.

In each case the VH or VL domains may be operably linked to their respective constant regions (CH or CL) where the constant regions are site-specific constant regions and provide a site-specific antibody. In selected embodiments the resulting site-specific antibody will comprise two unpaired cysteines in the CL domain.

For long-term, high-yield production of recombinant proteins stable expression is preferred. Accordingly, cell lines that stably express the selected antibody may be engineered using standard art recognized techniques and form part of the invention. Rather than using expression vectors that contain viral origins of replication, host cells can be transformed with DNA controlled by appropriate expression control elements (e.g., promoter or enhancer sequences, transcription terminators, polyadenylation sites, etc.), and a selectable marker. Any of the selection systems well known in the art may be used, including the glutamine synthetase gene expression system (the GS system) which provides an efficient approach for enhancing expression under selected conditions. The GS system is discussed in whole or part in connection with EP 0 216 846, EP 0 256 055, EP 0 323 997 and EP 0 338 841 and U.S. Pat. Nos. 5,591,639 and 5,879,936. Another compatible expression system for the development of stable cell lines is the Freedom™ CHO-S Kit (Life Technologies).

Once an antibody of the invention has been produced by recombinant expression or any other of the disclosed techniques, it may be purified or isolated by methods known in the art in that it is identified and separated and/or recovered from its natural environment and separated from contaminants that would interfere with diagnostic or therapeutic uses for the antibody or related ADC. Isolated antibodies include antibodies in situ within recombinant cells.

These isolated preparations may be purified using various art-recognized techniques, such as, for example, ion exchange and size exclusion chromatography, dialysis, diafiltration, and affinity chromatography, particularly Protein A or Protein G affinity chromatography.

Antibody Conjugates

As discussed above the antibody of the invention is conjugated with two calicheamicin toxins to form an "antibody drug conjugate" (ADC) or "antibody conjugate". The term "conjugate" is used broadly and means the covalent association of a calicheamicin with the antibody of the instant invention. Herein the association is effected through cysteine residues at position 214 of the light chain constant regions.

It will be appreciated that the ADCs of the instant invention may be used to selectively deliver predetermined calicheamicin warheads to tumorigenic cells and/or cells expressing SEZ6. As set forth herein the terms "drug" or "warhead" may be used interchangeably and will mean a calicheamicin molecule. A "payload" comprises the calicheamicin in combination with a non-cleavable linker compound that provides a stable pharmaceutical complex until the ADC reaches the target. Formula II (set forth above) is an exemplary payload with a calicheamicin warhead.

In preferred embodiments the disclosed ADC will direct the bound payload (e.g., Formula II) to the target site in a relatively unreactive, non-toxic state before releasing and activating the calicheamicin toxin. This targeted release of the warhead is preferably achieved through stable conjugation of the payloads and relatively homogeneous composition of the ADC preparations which minimize over-conjugated toxic ADC species. Coupled with a particularly stable non-cleavable drug linker that is designed to release the warhead upon delivery to the tumor site, the conjugates of the instant invention can substantially reduce undesirable non-specific toxicity. This advantageously provides for relatively high levels of the active cytotoxin at the tumor site while minimizing exposure of non-targeted cells and tissue thereby providing enhanced efficacy.

The conjugate of the instant invention may be generally represented by Formula III:

wherein:

a) Ab comprises an anti-SEZ6 antibody having a heavy chain of SEQ ID NO:3 and a light chain of SEQ ID NO:4;

b) [L-D] comprises the linker drug of Formula II covalently attached to Ab; and c) n is 2.

In some preferred embodiments the instant invention comprises selective conjugation of the calicheamicin payload to free cysteines using stabilization agents in combination with mild reducing agents as described herein. Such reaction conditions tend to provide more homogeneous preparations with less non-specific conjugation and contaminants and correspondingly less toxicity.

Calicheamicin Warhead

As discussed herein the antibodies of the invention are conjugated to a calicheamicin toxin. That is, the disclosed SEZ6 ADC of the invention may comprise the formula Ab-[L-D]n (Formula III) or a pharmaceutically acceptable salt thereof wherein D is calicheamicin or analog thereof in any of the molecular structures provided herein. As known in the art the calicheamicins are a class of enediyne antitumor antibiotics derived from the bacterium *Micromonospora echinospora*, including calicheamicin $\gamma_1^I$, calicheamicin calicheamicin $\beta_1^{Br}$, calicheamicin $\alpha_2^I$, calicheamicin $\alpha_3^I$, calicheamicin $\beta_1^i$ and calicheamicin $\delta_1^i$ were isolated and characterized. The structures of each of the foregoing calicheamicin analogs are well known in the art (e.g., see Lee et al., Journal of Antibiotics, July 1989 which is incorporated herein by reference in its entirety) and are compatible with the calicheamicin drug linker constructs and antibody drug conjugates disclosed herein.

In general, calicheamicin $\gamma^1$ contains two distinct structural regions, each playing a specific role in the compound's biological activity. The larger of the two consists of an extended sugar residue, comprising four monosaccharide units and one hexasubstituted benzene ring; these are joined together through a highly unusual series of glycosidic, thioester, and hydroxylamine linkages. The second structural region, the aglycon (known as calicheamicinone), contains a compact, highly functionalized bicyclic core, housing a strained enediyne unit within a bridging 10-member ring. This aglycon subunit further comprises an allylic trisulfide which, as described below, functions as an activator to generate the cytotoxic form of the molecule.

By way of example the structure for trisulfide calicheamicin $\gamma_1^I$ is shown immediately below in Formula IV:

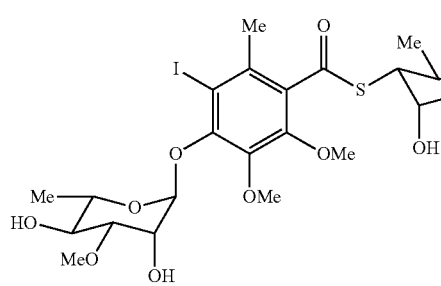
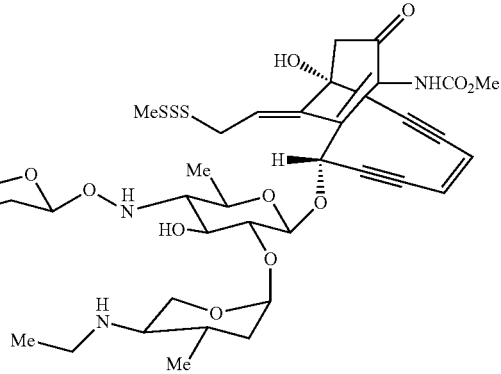

Formula IV

As used herein the term "calicheamicin" shall be held to mean any one of calicheamicin $\gamma_1^I$, calicheamicin calicheamicin $\beta_1^{Br}$, calicheamicin $\gamma_1^{Br}$, calicheamicin $\alpha_2^I$, calicheamicin $\beta_1^i$ and calicheamicin $\delta_1$ along with N-acetyl derivatives, sulfide analogs and analogs thereof. Accordingly, as used herein, the term "calicheamicin" will be understood to encompass any calicheamicin found in nature as well as calicheamicin molecules with a disulfide moiety having a point of attachment to another molecule (e.g., an antibody drug conjugate) and analogs thereof. By way of example, as used herein, calicheamicin $\gamma^1$ is to be construed as comprising the following molecules:

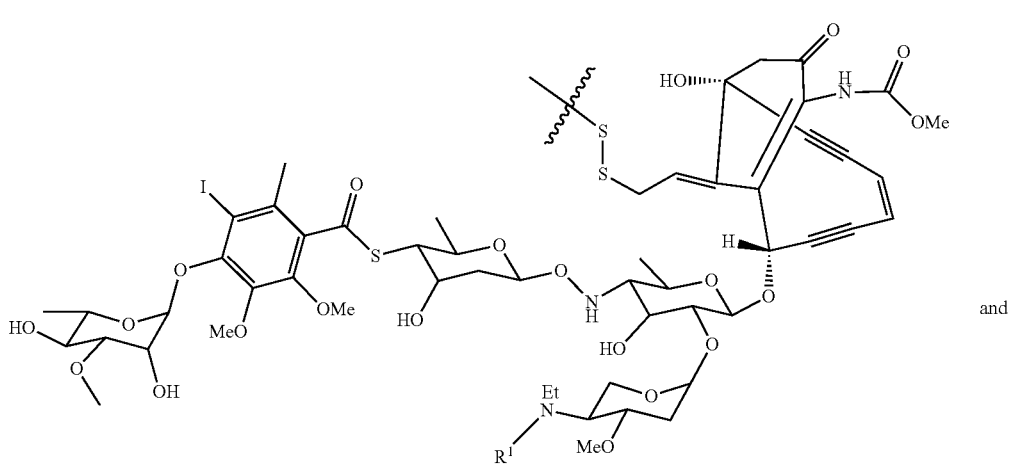

Formula V and

Formula VI

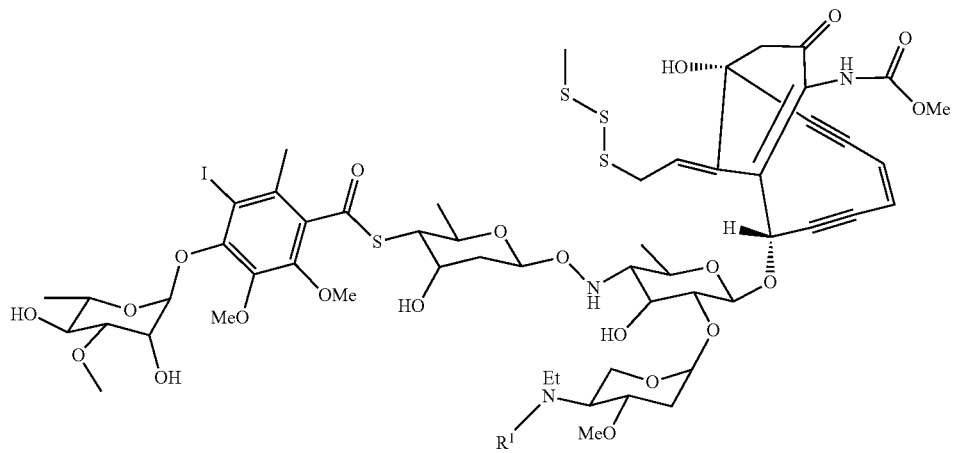

wherein R¹ is defined as below.

It will be appreciated that any of the aforementioned compounds are compatible with the teachings herein and may be used to fabricate the disclosed calicheamicin drug linker constructs and antibody drug conjugates. In certain embodiments, such as shown in Formula II, the calicheamicin component of the disclosed antibody drug conjugates will comprise N-acetyl Calicheamicin $\gamma_1^I$ (N-Ac calicheamicin).

Calicheamicins target nucleic acids and cause strand scission thereby killing the target cell. More specifically, calicheamicins have been found to bind the minor groove of DNA, where they then undergo a reaction analogous to Bergman cyclization to generate a diradical species. In this regard the aryl tetrasaccharide subunit serves to deliver the drug to its target, tightly binding to the minor groove of double helical DNA as demonstrated by Crothers et al. (1999). When a nucleophile (e.g. glutathione) attacks the central sulfur atom of the trisulfide group, it causes a significant change in structural geometry and imposes a great deal of strain on the 10-member enediyne ring. This strain is completely relieved by the enediyne undergoing a cycloaromatization reaction, generating a highly-reactive 1,4-benzenoid diradical and leading, eventually, to DNA cleavage by attracting hydrogen atoms from the deoxyribose DNA backbone which results in strand scission. Note that in the calicheamicin disulfide analog constructs of the instant invention the nucleophile cleaves the protected disulfide bond to produce the desired diradical.

More particularly it is understood that D expressly comprises any member of the class of calicheamicin as known in the art wherein the terminal —S—S—S—CH₃ moiety may be replaced with —S—S$\xi$, wherein the symbol $\xi$ represents the point of attachment to a linker.

Thus, in certain embodiments, D is of the Formula V,

Formula V

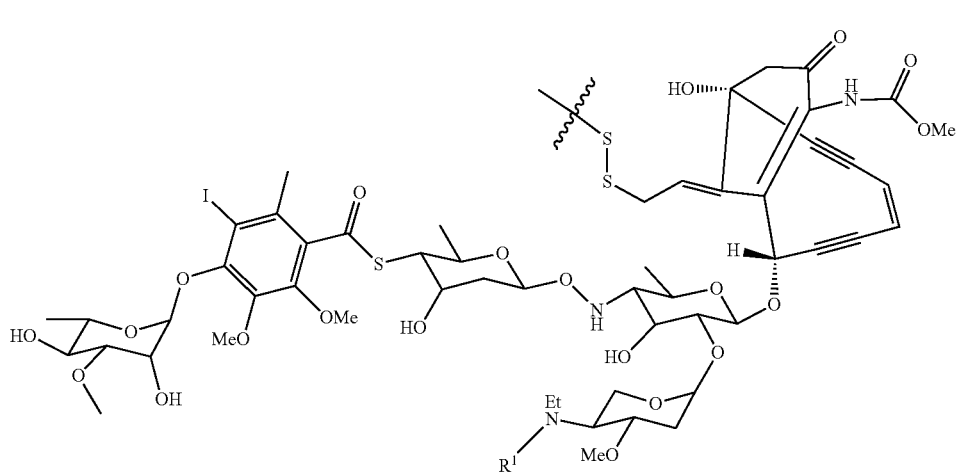

wherein R¹ is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, —CF₃, —CCl₃, —CBr₃, —CI₃, —CN, —C(O)R$^{1E}$, —NR$^{1B}$R$^{1C}$, —C(O)OR$^{1A}$, —C(O)NR$^{1B}$R$^{1C}$, —SO$_{n1}$R$^{1B}$ or —SO$_{v1}$NR$^{1B}$R$^{1C}$. In certain selected embodiments R¹ will comprise H. In other selected embodiments R¹ will comprise —C(O)CH₃.

R$^{1A}$, R$^{1B}$, R$^{1C}$, R$^{1D}$ and R$^{1E}$ are independently hydrogen, halogen, —CF₃, —CCl₃, —CBr₃, —CI₃, —OH, —NH₂, —COOH, —CONH₂, —N(O)₂, —SH, —S(O)₃H, —S(O)₄H, —S(O)₂NH₂, —NHNH₂, —ONH₂, —NHC(O)NHNH₂, —NHC(O)NH₂, —NHS(O)₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^{1B}$ and $R^{1C}$ substituents bonded to the same nitrogen atom may optionally be joined to form a substituted or unsubstituted heterocycloalkyl or substituted or unsubstituted heteroaryl. The symbol n1 is independently an integer from 0 to 4, the symbol v1 is independently 1 or 2 and the symbol ⌇ represents the point of attachment to a linker.

cleavable linker associating the warheads with the antibody targeting agent. Compatible non-cleavable linkers covalently bind with the reactive residue on the antibody (preferably a cysteine or lysine) and calicheamicin through the disulfide moiety.

In particularly preferred embodiments the linker will comprise selected non-cleavable linkers. In certain embodiments the ADCs will comprise compatible non-cleavable linkers containing amide linked polyethylene glycol or alkyl spacers that liberate the calicheamicin payload during lysosomal degradation of the ADC within the target cell. A particularly compatible non-cleavable linker used in Formula II is shown immediately below in Formula VII wherein the wavy line indicates the point of attachment to the disulfide group of the calicheamicin.

Formula VII

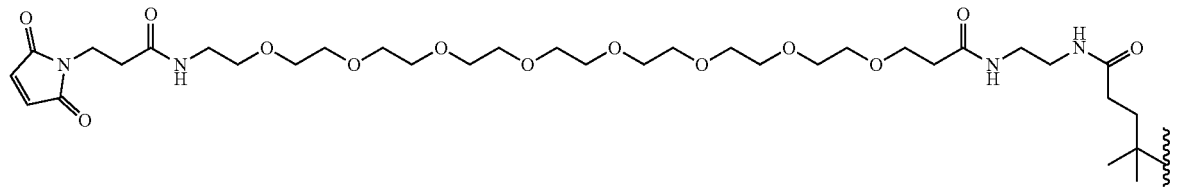

With regard to Formula V it will be appreciated that the illustrated compound comprises a disulfide calicheamicin analog (e.g., an N-acetyl calicheamicin analog such as shown in Formula II) preferably bound to a disulfide protective group (at the point of attachment represented by ⌇) that is covalently bound to the remainder of the linker. The disulfide protective group improves stability of the disulfide bond in the bloodstream and allows for effective synthesis of the disclosed calicheamicin-linker constructs. In certain embodiments the calicheamicin disulfide group is preferably protected by a short chain substituted or unsubstituted bifunctional aliphatic or aryl group ("disulfide protective group") that provides stability (e.g., plasma stability) until the ADC reaches the target cell. More specifically the configuration of the disulfide protective group provides a degree of steric hindrance for the disulfide bond thereby reducing its susceptibility to cleavage via thiol-disulfide exchange reactions. In this position the disulfide protective group covalently links the calicheamicin disulfide group with the remainder of the non-cleavable linker.

Upon reaching the target (e.g., a cancer cell) the linker will preferably be severed or degraded to release the calicheamicin attached to part of the linker through the disulfide protective group. In certain embodiments once the linker has been initially cleaved beyond the disulfide protective group (i.e. distal from the calicheamicin) the remainder of the linker attached to the calicheamicin will be degraded under physiological conditions to the point where the disulfide bond is severed (preferably intracellularly) followed by rearrangement and formation of the active biradical calicheamicin species. It is this form of the calicheamicin warhead that binds to the minor groove of the cellular DNA and induces the desired cytotoxic effects (See Walker et al., Biochemistry 89: 4608-4612, 5/92 which is incorporated herein by reference).

Linker Compounds

As indicated above payloads compatible with the instant invention comprise one or more warheads and a non- Synthesis of Formula II, including the linker component, is shown in Example 3 below with attendant conditions.

Conjugation

Various methods are known in the art for conjugating a therapeutic compound to a cysteine residue and will be apparent to the skilled artisan. Under basic conditions the cysteine residues will be deprotonated to generate a thiolate nucleophile which may be reacted with soft electrophiles such as maleimides and iodoacetamides. Generally, reagents for such conjugations may react directly with a cysteine thiol to form the conjugated protein or with a linker drug to form a linker drug intermediate. In the case of a linker, several routes, employing organic chemistry reactions, conditions, and reagents are known to those skilled in the art, including: (1) reaction of a cysteine group of the protein of the invention with a linker reagent, to form a protein-linker intermediate, via a covalent bond, followed by reaction with an activated compound; and (2) reaction of a nucleophilic group of a compound with a linker reagent, to form a drug linker intermediate, via a covalent bond, followed by reaction with a cysteine group of a protein of the invention.

Prior to conjugation, antibodies may be made reactive for conjugation with linker reagents by treatment with a reducing agent such as dithiothreitol (DTT) or (tris(2-carboxyethyl)phosphine (TCEP). In other embodiments additional nucleophilic groups can be introduced into antibodies through the reaction of lysines with reagents, including but not limited to, 2-iminothiolane (Traut's reagent), SATA, SATP or SAT(PEG)4, resulting in conversion of an amine into a thiol.

Conjugation reagents commonly include maleimide, haloacetyl, iodoacetamide succinimidyl ester, isothiocyanate, sulfonyl chloride, 2,6-dichlorotriazinyl, pentafluorophenyl ester, and phosphoramidite, although other functional groups can also be used. In certain embodiments methods include, for example, the use of maleimides, iodoacetimides or haloacetyl/alkyl halides, aziridine, acryloyl derivatives to react with the thiol of a cysteine to produce a thioether that is reactive with a compound. Disulphide exchange of a free thiol with an activated piridyldisulphide is also useful for producing a conjugate (e.g., use of 5-thio-2-nitrobenzoic (TNB) acid). Preferably, a maleimide is used.

As discussed above site-specific antibodies or engineered antibodies allow for conjugate preparations that exhibit enhanced stability and substantial homogeneity due, at least in part, to the provision of engineered free cysteine site(s) and/or the novel conjugation procedures set forth herein. Unlike conventional conjugation methodology that fully or partially reduces each of the intrachain or interchain antibody disulfide bonds to provide conjugation sites (and is fully compatible with the instant invention), the present invention additionally provides for the selective reduction of certain prepared free cysteine sites and attachment of the drug linker to the same.

In this regard it will be appreciated that the conjugation specificity promoted by the engineered sites and the selective reduction allows for a high percentage of site directed conjugation at the desired positions. Significantly some of these conjugation sites, such as those present in the terminal region of the light chain constant region, are typically difficult to conjugate effectively as they tend to cross-react with other free cysteines. However, through molecular engineering and selective reduction of the resulting free cysteines, efficient conjugation rates may be obtained which considerably reduces unwanted high-DAR contaminants and non-specific toxicity. More generally the engineered constructs and disclosed novel conjugation methods comprising selective reduction provide ADC preparations having improved pharmacokinetics and/or pharmacodynamics and, potentially, an improved therapeutic index.

In certain embodiments site-specific constructs present free cysteine(s) which, when reduced, comprise thiol groups that are nucleophilic and capable of reacting to form covalent bonds with electrophilic groups on linker moieties such as those disclosed above. As discussed above antibodies of the instant invention preferably have reducible unpaired interchain cysteines, i.e. cysteines providing such nucleophilic groups. Thus, in certain embodiments the reaction of free sulfhydryl groups of the reduced free cysteines and the terminal maleimido or haloacetamide groups of compatible drug linkers will provide the desired conjugation. In such cases free cysteines of the antibodies may be made reactive for conjugation with linker reagents by treatment with a reducing agent such as dithiothreitol (DTT) or (tris (2-carboxyethyl) phosphine (TCEP). Each free cysteine will thus present, theoretically, a reactive thiol nucleophile. While such reagents are particularly compatible with the instant invention it will be appreciated that conjugation of site-specific antibodies may be achieved using various reactions, conditions and reagents generally known to those skilled in the art.

In addition, it has been found that the free cysteines of engineered antibodies may be selectively reduced to provide enhanced site-directed conjugation and a reduction in unwanted, potentially toxic contaminants. More specifically "stabilizing agents" such as arginine have been found to modulate intra- and inter-molecular interactions in proteins and may be used, in conjunction with selected reducing agents (preferably relatively mild), to selectively reduce the free cysteines and to facilitate site-specific conjugation as set forth herein. As used herein the terms "selective reduction" or "selectively reducing" may be used interchangeably and shall mean the reduction of free cysteine(s) without substantially disrupting native disulfide bonds present in the engineered antibody. In selected embodiments this selective reduction may be effected by the use of certain reducing agents or certain reducing agent concentrations. In other embodiments selective reduction of an engineered construct will comprise the use of stabilization agents in combination with reducing agents (including mild reducing agents). It will be appreciated that the term "selective conjugation" shall mean the conjugation of an engineered antibody that has been selectively reduced in the presence of a cytotoxin as described herein. In this respect the use of such stabilizing agents (e.g., arginine) in combination with selected reducing agents can markedly improve the efficiency of site-specific conjugation as determined by extent of conjugation on the heavy and light antibody chains and DAR distribution of the preparation. Compatible antibody constructs and selective conjugation techniques and reagents are extensively disclosed in WO2015/031698 which is incorporated herein specifically as to such methodology and constructs.

While not wishing to be bound by any particular theory, such stabilizing agents may act to modulate the electrostatic microenvironment and/or modulate conformational changes at the desired conjugation site, thereby allowing relatively mild reducing agents (which do not materially reduce intact native disulfide bonds) to facilitate conjugation at the desired free cysteine site(s). Such agents (e.g., certain amino acids) are known to form salt bridges (via hydrogen bonding and electrostatic interactions) and can modulate protein-protein interactions in such a way as to impart a stabilizing effect that may cause favorable conformational changes and/or reduce unfavorable protein-protein interactions. Moreover, such agents may act to inhibit the formation of undesired intramolecular (and intermolecular) cysteine-cysteine bonds after reduction thus facilitating the desired conjugation reaction wherein the engineered site-specific cysteine is bound to the drug (preferably via a linker). Since selective reduction conditions do not provide for the significant reduction of intact native disulfide bonds, the subsequent conjugation reaction is naturally driven to the relatively few reactive thiols on the free cysteines (e.g., preferably 2 free thiols per antibody). As previously alluded to, such techniques may be used to considerably reduce levels of non-specific conjugation and corresponding unwanted DAR species in conjugate preparations fabricated in accordance with the instant disclosure.

In selected embodiments stabilizing agents compatible with the present invention will generally comprise compounds with at least one moiety having a basic pKa. In certain embodiments the moiety will comprise a primary amine while in other embodiments the amine moiety will comprise a secondary amine. In still other embodiments the amine moiety will comprise a tertiary amine or a guanidinium group. In other selected embodiments the amine moiety will comprise an amino acid while in other compatible embodiments the amine moiety will comprise an amino acid side chain. In yet other embodiments the amine moiety will comprise a proteinogenic amino acid. In still other embodiments the amine moiety comprises a non-proteinogenic amino acid. In some embodiments, compatible stabilizing agents may comprise arginine, lysine, proline and cysteine. In certain preferred embodiments the stabilizing agent will comprise arginine. In addition, compatible stabilizing agents may include guanidine and nitrogen containing heterocycles with basic pKa.

In certain embodiments compatible stabilizing agents comprise compounds with at least one amine moiety having a pKa of greater than about 7.5, in other embodiments the subject amine moiety will have a pKa of greater than about 8.0, in yet other embodiments the amine moiety will have a pKa greater than about 8.5 and in still other embodiments the stabilizing agent will comprise an amine moiety having a pKa of greater than about 9.0. Other embodiments will comprise stabilizing agents where the amine moiety will have a pKa of greater than about 9.5 while certain other embodiments will comprise stabilizing agents exhibiting at least one amine moiety having a pKa of greater than about 10.0. In still other embodiments the stabilizing agent will comprise a compound having the amine moiety with a pKa of greater than about 10.5, in other embodiments the stabilizing agent will comprise a compound having an amine moiety with a pKa greater than about 11.0, while in still other embodiments the stabilizing agent will comprise an amine moiety with a pKa greater than about 11.5. In yet other embodiments the stabilizing agent will comprise a compound having an amine moiety with a pKa greater than about 12.0, while in still other embodiments the stabilizing agent will comprise an amine moiety with a pKa greater than about 12.5. Those of skill in the art will understand that relevant pKa's may readily be calculated or determined using standard techniques and used to determine the applicability of using a selected compound as a stabilizing agent.

The disclosed stabilizing agents are shown to be particularly effective at targeting conjugation to free site-specific cysteines when combined with certain reducing agents. For the purposes of the instant invention, compatible reducing agents may include any compound that produces a reduced free site-specific cysteine for conjugation without significantly disrupting the native disulfide bonds of the engineered antibody. Under such conditions, preferably provided by the combination of selected stabilizing and reducing agents, the activated drug linker is largely limited to binding to the desired free site-specific cysteine site(s). Relatively mild reducing agents or reducing agents used at relatively low concentrations to provide mild conditions are particularly preferred. As used herein the terms "mild reducing agent" or "mild reducing conditions" shall be held to mean any agent or state brought about by a reducing agent (optionally in the presence of stabilizing agents) that provides thiols at the free cysteine site(s) without substantially disrupting native disulfide bonds present in the engineered antibody. That is, mild reducing agents or conditions (preferably in combination with a stabilizing agent) are able to effectively reduce free cysteine(s) (provide a thiol) without significantly disrupting the protein's native disulfide bonds. The desired reducing conditions may be provided by a number of sulfhydryl-based compounds that establish the appropriate environment for selective conjugation. In embodiments mild reducing agents may comprise compounds having one or more free thiols while in some embodiments mild reducing agents will comprise compounds having a single free thiol. Non-limiting examples of reducing agents compatible with the selective reduction techniques of the instant invention comprise glutathione, n-acetyl cysteine, cysteine, 2-aminoethane-1-thiol and 2-hydroxyethane-1-thiol.

It will further be appreciated that engineered antibodies capable of conjugation may contain free cysteine residues that comprise sulfhydryl groups that are blocked or capped as the antibody is produced or stored. Such caps include small molecules, proteins, peptides, ions and other materials that interact with the sulfhydryl group and prevent or inhibit conjugate formation. In some cases the unconjugated engineered antibody may comprise free cysteines that bind other free cysteines on the same or different antibodies. As discussed herein such cross-reactivity may lead to various contaminants during the fabrication procedure. In some embodiments, the engineered antibodies may require uncapping prior to a conjugation reaction. In specific embodiments, antibodies herein are uncapped and display a free sulfhydryl group capable of conjugation. In specific embodiments, antibodies herein are subjected to an uncapping reaction that does not disturb or rearrange the naturally occurring disulfide bonds. It will be appreciated that in most cases the uncapping reactions will occur during the normal reduction reactions (reduction or selective reduction).

DAR Distribution and Purification

In selected embodiments conjugation and purification methodology compatible with the present invention advantageously provides the ability to generate relatively homogeneous ADC preparations comprising a narrow DAR distribution. In this regard the disclosed constructs (e.g., site-specific constructs) and/or selective conjugation provides for homogeneity of the ADC species within a sample in terms of the stoichiometric ratio between the drug and the engineered antibody and with respect to the toxin location. As briefly discussed above the term "drug to antibody ratio" or "DAR" refers to the molar ratio of drug to antibody in an ADC preparation. In certain embodiments a conjugate preparation may be substantially homogeneous with respect to its DAR distribution, meaning that within the ADC preparation is a predominant species of site-specific ADC with a particular drug loading (e.g., a drug loading of 2) that is also uniform with respect to the site of loading (i.e., on the free cysteines). In other certain embodiments of the invention it is possible to achieve the desired homogeneity through the use of site-specific antibodies and/or selective reduction and conjugation. In other embodiments the desired homogeneity may be achieved through the use of site-specific constructs in combination with selective reduction. In yet other embodiments compatible preparations may be purified using analytical or preparative chromatography techniques to provide the desired homogeneity. In each of these embodiments the homogeneity of the ADC sample can be analyzed using various techniques known in the art including but not limited to mass spectrometry, HPLC (e.g. size exclusion HPLC, RP-HPLC, HIC-HPLC etc.) or capillary electrophoresis.

With regard to the purification of ADC preparations it will be appreciated that standard pharmaceutical preparative methods may be employed to obtain the desired purity. As discussed herein liquid chromatography methods such as reverse phase (RP) and hydrophobic interaction chromatography (HIC) may separate compounds in the mixture by drug loading value. In some cases, ion-exchange (IEC) or mixed-mode chromatography (MMC) may also be used to isolate species with a specific drug load.

In any event the disclosed ADCs and preparations thereof may comprise drug and antibody moieties in various stoichiometric molar ratios depending on the configuration of the antibody and, at least in part, on the method used to effect conjugation. In certain preferred embodiments the drug loading per ADC may comprise 2 calicheamicin warheads.

Despite the relatively high level of homogeneity provided by the instant invention the disclosed compositions actually comprise a mixture of conjugates with a range of drug compounds. As such, the disclosed ADC compositions include mixtures of conjugates where most of the constituent antibodies are covalently linked to one or more drug moieties and (despite the relative conjugate specificity provided by engineered constructs and selective reduction) where the drug moieties may be attached to the antibody by various thiol groups. That is, following conjugation, compositions of the invention will comprise a mixture of ADCs with different drug loads at various concentrations (along with certain reaction contaminants primarily caused by free cysteine cross reactivity). However, using selective reduction and post-fabrication purification the conjugate compositions may be driven to the point where they largely contain a single predominant desired ADC species (e.g., with a drug loading of 2) with relatively low levels of other ADC species (e.g., with a drug loading of 1, 4, 6, etc.). The average DAR value represents the weighted average of drug loading for the composition as a whole (i.e., all the ADC species taken together). Those of skill in the art will appreciate that acceptable DAR values or specifications are often presented as an average, a range or distribution (i.e., an average DAR of 2+/−0.5). Preferably compositions comprising a measured average DAR within the range (i.e., 1.5 to 2.5) would be used in a pharmaceutical setting.

Thus, in some embodiments the present invention will comprise compositions having an average DAR of 2+/−0.5. In other embodiments the present invention will comprise an average DAR of 2+/−0.4 or a DAR of 2+/−0.3 or a DAR of 2+/−0.2. In other embodiments IgG1 conjugate compositions will preferably comprise a composition with relatively low levels (i.e., less than 30%) of non-predominant ADC species (e.g., ADCs with a drug loading of 0, 1, 3, 4, 5, etc.). In some embodiments the ADC composition will comprise an average DAR of 2+/−0.4 with relatively low levels (<30%) of non-predominant ADC species. In some embodiments the ADC composition will comprise an average DAR of 2+/−0.3 with relatively low levels (<30%) of non-predominant ADC species. In yet other embodiments the predominant ADC species (e.g., with a drug loading of 2) will be present at a concentration of greater than 50%, at a concentration of greater than 55%, at a concentration of greater than 60%, at a concentration of greater than 65%, at a concentration of greater than 70%, at a concentration of greater than 75%, at a concentration of greater that 80%, at a concentration of greater than 85%, at a concentration of greater than 90%, at a concentration of greater than 93%, at a concentration of greater than 95% or even at a concentration of greater than 97% when measured against all other DAR species present in the composition.

As detailed in the Examples below the distribution of drugs per antibody in preparations of ADC from conjugation reactions may be characterized by conventional means such as UV-Vis spectrophotometry, reverse phase HPLC, HIC, mass spectroscopy, ELISA, and electrophoresis. The quantitative distribution of ADC in terms of drugs per antibody may also be determined.

Pharmaceutical Preparations and Therapeutic Uses

The antibodies or ADCs of the invention can be formulated in various ways using art recognized techniques. In some embodiments, the therapeutic compositions of the invention can be administered neat or with a minimum of additional components while others may optionally be formulated to contain suitable pharmaceutically acceptable carriers. As used herein, "pharmaceutically acceptable carriers" comprise excipients, vehicles, adjuvants and diluents that are well known in the art.

Dosages and Dosing Regimens

The particular dosage regimen, i.e., dose, timing and repetition, will depend on the particular individual, as well as empirical considerations such as pharmacokinetics (e.g., half-life, clearance rate, etc.). Determination of the frequency of administration may be made by persons skilled in the art, such as an attending physician based on considerations of the condition and severity of the condition being treated, age and general state of health of the subject being treated and the like. Frequency of administration may be adjusted over the course of therapy based on assessment of the efficacy of the selected composition and the dosing regimen. Such assessment can be made on the basis of markers of the specific disease, disorder or condition. In embodiments where the individual has cancer, these include direct measurements of tumor size via palpation or visual observation; indirect measurement of tumor size by x-ray or other imaging techniques; an improvement as assessed by direct tumor biopsy and microscopic examination of a tumor sample; the measurement of an indirect tumor marker or an antigen identified according to art-recognized techniques; reduction in the number of proliferative or tumorigenic cells, maintenance of the reduction of such neoplastic cells; reduction of the proliferation of neoplastic cells; or delay in the development of metastasis.

Indications

The invention provides for the use of an ADC of the invention for the treatment of various neoplastic disorders. In certain embodiments the diseases to be treated are neoplastic conditions comprising solid tumors. In selected embodiments the ADC of the invention will be used to treat tumors or tumorigenic cells expressing a SEZ6 determinant. In certain other embodiments the disclosed ADC will be used to treat a subject suffering from small cell lung cancer (SCLC). Preferably the "subject" or "patient" to be treated will be human although, as used herein, the terms are expressly held to comprise any mammalian species.

In selected embodiments the ADC can be administered to small cell lung cancer patients exhibiting limited stage disease or extensive stage disease. In other embodiments the disclosed ADC will be administered to refractory patients (i.e., those whose disease recurs during or shortly after completing a course of initial therapy); sensitive patients (i.e., those whose relapse is longer than 2-3 months after primary therapy); or patients exhibiting resistance to a platinum based agent (e.g. carboplatin, cisplatin, oxaliplatin) and/or a taxane (e.g. docetaxel, paclitaxel, larotaxel or cabazitaxel). In certain preferred embodiments the SEZ6 ADC of the instant invention may be administered to frontline patients. In other embodiments the SEZ6 ADC of the instant invention may be administered to second line patients. In still other embodiments the SEZ6 ADC of the instant invention may be administered to third line patients or to fourth line patients.

Articles of Manufacture

The invention includes pharmaceutical packs and kits comprising one or more containers or receptacles, wherein a container can comprise one or more doses of the ADC of the invention. In certain embodiments, the pack or kit contains a unit dosage, meaning a predetermined amount of a composition comprising, for example, the ADC of the invention, with or without one or more additional agents and optionally, one or more anti-cancer agents.

When the components of the kit are provided in one or more liquid solutions, aqueous or non-aqueous though typically an aqueous solution is preferred, with a sterile aqueous solution being particularly preferred. The formulation in the kit can also be provided as dried powder(s) or in lyophilized form that can be reconstituted upon addition of an appropriate liquid. The liquid used for reconstitution can be contained in a separate container. Such liquids can comprise sterile, pharmaceutically acceptable buffer(s) or other diluent(s) such as bacteriostatic water for injection. Where the kit comprises the ADC of the invention in combination with additional therapeutics or agents, the solution may be pre-mixed, either in a molar equivalent combination, or with one component in excess of the other. Alternatively, the ADC of the invention and any optional anti-cancer agent or other agent can be maintained separately within distinct containers prior to administration to a patient.

In certain preferred embodiments the aforementioned kits, incorporating compositions of the invention will comprise a label, marker, package insert, bar code and/or reader indicating that the kit contents may be used for the treatment of cancer. In other preferred embodiments the kit may comprise a label, marker, package insert, bar code and/or reader indicating that the kit contents may be administered in accordance with a certain dosage or dosing regimen to treat a subject suffering from cancer. In other particularly preferred aspects the label, marker, package insert, bar code and/or reader indicates that the kit contents may be used for the treatment of small cell lung cancer or a dosing regimen for treatment of the same.

Suitable containers or receptacles include, for example, bottles, vials, syringes, infusion bags (i.v. bags), etc. The containers can be formed from a variety of materials such as glass or pharmaceutically compatible plastics. In certain embodiments the receptacle(s) can comprise a sterile access port. For example, the container may be an intravenous solution bag or a vial having a stopper that can be pierced by a hypodermic injection needle.

In some embodiments the kit can contain a means by which to administer the ADC and any optional components to a patient, e.g., one or more needles or syringes (pre-filled or empty), or other such like apparatus, from which the formulation may be injected or introduced into the subject or applied to a diseased area of the body. The kits of the invention will also typically include a means for containing the vials, or such like, and other components in close confinement for commercial sale, such as, e.g., blow-molded plastic containers into which the desired vials and other apparatus are placed and retained.

Miscellaneous

Unless otherwise defined herein, scientific and technical terms used in connection with the invention shall have the meanings that are commonly understood by those of ordinary skill in the art. Further, unless otherwise required by context, singular terms shall include pluralities and plural terms shall include the singular. In addition, ranges provided in the specification and appended claims include both end points and all points between the end points. Therefore, a range of 2.0 to 3.0 includes 2.0, 3.0, and all points between 2.0 and 3.0.

Generally, techniques of cell and tissue culture, molecular biology, immunology, microbiology, genetics and chemistry described herein are those well-known and commonly used in the art. The nomenclature used herein, in association with such techniques, is also commonly used in the art. The methods and techniques of the invention are generally performed according to conventional methods well known in the art and as described in various references that are cited throughout the present specification unless otherwise indicated.

REFERENCES

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference, regardless of whether the phrase "incorporated by reference" is or is not used in relation to the particular reference. The foregoing detailed description and the examples that follow have been given for clarity of understanding only. No unnecessary limitations are to be understood therefrom. The invention is not limited to the exact details shown and described. Variations obvious to one skilled in the art are included in the invention defined by the claims. Any section headings used herein are for organizational purposes only and are not to be construed as limiting the subject matter described.

8. EXAMPLES

The invention, generally described above, will be understood more readily by reference to the following examples, which are provided by way of illustration and are not intended to be limiting of the instant invention. The examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

Sequence Listing Summary

TABLE 2 provides a summary of amino acid and nucleic acid sequences included herein.

TABLE 2

| SEQ ID NO | Description |
| --- | --- |
| 1 | Seizure protein 6 homolog isoform 1 precursor (NP_849191) |

TABLE 2-continued

| SEQ ID NO | Description |
| --- | --- |
| 2 | Seizure protein 6 homolog isoform 2 precursor (NP_001092105) |
| 3 | hSEZ6-1.ss1 heavy chain protein sequence |
| 4 | hSEZ6-1.ss1 light chain protein sequence |
| 5 | Nucleic acid sequence encoding hSEZ6-1.ss1 heavy chain protein sequence including introns |
| 6 | Nucleic acid sequence encoding hSEZ6-1.ss1 light chain protein sequence |

Example 1: Generation of a SEZ6 Antibody

SEZ6 murine antibodies were produced in accordance with the teachings herein through inoculation with human SEZ6-Fc. In this regard three strains of mice were used to generate high affinity, murine, monoclonal antibody modulators that can be used to associate with and/or inhibit the action of human SEZ6 (e.g., NP_849191: Seizure protein 6 homolog isoform 1 precursor; NP_001092105: Seizure protein 6 homolog isoform 2 precursor) for the prevention and/or treatment of various proliferative disorders. Specifically, Balb/c, CD-1 and FVB mouse strains were immunized with human recombinant SEZ6-Fc and used to produce Hybridomas.

The SEZ6-Fc antigen was purified from supernatant from CHO-S cells over expressing a SEZ6-Fc construct. 10 μg of SEZ6-Fc immunogen was used for the first immunization, followed by 5 μg and 2.5 μg of SEZ6-Fc immunogen for the subsequent three immunizations and five immunizations, respectively. All immunizations were performed with the immunogen emulsified with an equal volume of TITER-MAX® Gold (CytRx Corporation) or alum adjuvant. Murine antibodies were generated by immunizing six female mice (two each of: Balb/c, CD-1, FVB) via footpad route for all injections.

Solid-phase ELISA assays were used to screen mouse sera for mouse IgG antibodies specific for human SEZ6. A positive signal above background was indicative of antibodies specific for SEZ6. Briefly, 96 well plates (VWR International, Cat. #610744) were coated with recombinant SEZ6-His at 0.5 μg/ml in ELISA coating buffer overnight. After washing with PBS containing 0.02% (v/v) Tween 20, the wells were blocked with 3% (w/v) BSA in PBS, 200 μL/well for 1 hour at room temperature (RT). Mouse serum was titrated (1:100, 1:200, 1:400, and 1:800) and added to the SEZ6 coated plates at 50 μL/well and incubated at RT for 1 hour. The plates are washed and then incubated with 50 μL/well HRP-labeled goat anti-mouse IgG diluted 1:10,000 in 3% BSA-PBS or 2% FCS in PBS for 1 hour at RT. Again the plates were washed and 40 μL/well of a TMB substrate solution (Thermo Scientific 34028) was added for 15 minutes at RT. After developing, an equal volume of 2N $H_2SO_4$ was added to stop substrate development and the plates were analyzed by spectrophotometer at OD 450.

Sera-positive immunized mice were sacrificed and draining lymph nodes (popliteal and inguinal, and medial iliac if enlarged) were dissected out and used as a source for antibody producing cells. A single cell suspension of B cells ($228.9 \times 10^6$ cells) was fused with non-secreting P3x63Ag8.653 myeloma cells (ATCC #CRL-1580) at a ratio of 1:1 by electrofusion. Electrofusion was performed using the BTX Hybrimmune™ System, (BTX Harvard Apparatus) as per the manufacturer's directions. After the fusion procedure the cells were resuspended in hybridoma selection medium supplemented with Azaserine (Sigma #A9666), high glucose DMEM medium with sodium pyruvate (Cellgro cat #15-017-CM) containing 15% Fetal Clone I serum (Hyclone), 10% BM Condimed (Roche Applied Sciences), 4 mM L-glutamine, 100 IU Penicillin-Streptomycin and 50 µM 2-mercaptoethanol and then plated in three T225 flasks in 90 mL selection medium per flask. The flasks were then placed in a humidified 37° C. incubator containing 5% $CO_2$ and 95% air for 6-7 days.

After six to seven days of growth the library consisting of the cells grown in bulk in the T225s was plated at 1 cell per well in Falcon 96 well U-bottom plates using the Aria I cell sorter. The selected hybridomas were then grown in 200 µL of culture medium containing 15% Fetal Clone I serum (Hyclone), 10% BM-Condimed (Roche Applied Sciences), 1 mM sodium pyruvate, 4 mM L-glutamine, 100 IU Penicillin-Streptomycin, 50 µM 2-mercaptoethanol, and 100 µM hypoxanthine Any remaining unused hybridoma library cells were frozen for future library testing. After ten to eleven days of growth supernatants from each well of the plated cells were assayed for antibodies reactive for SEZ6 by ELISA and FACS assays.

For screening by ELISA 96 well plates were coated with SEZ6-Fc at 0.3 µg/mL in PBS overnight at 4° C. The plates were washed and blocked with 3% BSA in PBS/Tween for one hour at 37° C. and used immediately or kept at 4° C. Undiluted hybridoma supernatants were incubated on the plates for one hour at RT. The plates were washed and probed with HRP labeled goat anti-mouse IgG diluted 1:10,000 in 3% BSA-PBS for one hour at RT. The plates were then incubated with substrate solution as described above and read at OD 450. Wells containing immunoglobulin that preferentially bound human SEZ6, as determined by a signal above background, were transferred and expanded.

Selected growth positive hybridoma wells secreting murine immunoglobulin were also screened for human SEZ6 specificity and cynomolgus, rat and murine SEZ6 cross reactivity using a flow cytometry based assay with 293 cells engineered to over-express the selected species specific antigen.

For the flow cytometry assays, $50 \times 10^4$ h293 cells transduced respectively with human, cynomolgus, rat or murine SEZ6 were incubated for 30 minutes with 25-100 µL hybridoma supernatant. Cells were washed with PBS, 2% FCS, twice and then incubated with 50 µL of a goat-anti-mouse IgG Fc fragment specific secondary conjugated to DyLight 649 diluted 1:200 in PBS/2% FCS. After 15 minutes of incubation, cells were washed twice with PBS, 2% FCS, and resuspended in the same buffer with DAPI and analyzed by flow cytometry using a FACSCanto II as per the manufacturer's instructions. Wells containing immunoglobulin that preferentially bound the SEZ6+ GFP+ cells were transferred and expanded. The resulting hSEZ6 specific clonal hybridomas were cryopreserved in CS-10 freezing medium (Biolife Solutions) and stored in liquid nitrogen. Antibodies that bound with human, cynomolgus, rat or murine SEZ6 cells were noted as cross-reactive.

ELISA and flow cytometry analysis confirmed that purified antibody from most or all of these hybridomas bound SEZ6 in a concentration-dependent manner. Wells containing immunoglobulin that bound SEZ6 GFP cells were transferred and expanded. The resulting clonal hybridomas were cryopreserved in CS-10 freezing medium (Biolife Solutions) and stored in liquid nitrogen.

One fusion was performed and seeded in 48 plates (4608 wells at approximately 40% cloning efficiency). The initial screen yielded sixty-three murine antibodies that associated with human SEZ6. A second screen was subsequently performed and yielded 134 antibodies that associated with human SEZ6.

Example 2: Fabrication of a Humanized Site-Specific SEZ6 Antibody

An antibody from Example 1 was chosen for further processing and humanization. RNA from the hybridoma expressing the selected antibody was isolated, amplified and sequenced using standard art-recognized techniques. From the nucleotide sequence information, data regarding V, D and J gene segments of the heavy and light chains of subject murine antibodies were obtained. The V-(D)-J sequences were aligned with mouse Ig germ line sequences and acceptor human variable framework regions were selected based on their highest sequence homology to the subject mouse framework sequence and its canonical structure for CDR grafting. The resulting genetic arrangement for the humanized variable regions of the antibody are shown in Table 3A immediately below.

TABLE 3A

| mAb | Human VH | Human JH | FW changes | Human VK | Human JK | FW changes |
|---|---|---|---|---|---|---|
| SEZ6-1 | IGHV5-51 | JH4 | none | IGKV-L6 | JK4 | none |

The engineered variable regions were then used to generate a human IgG1/kappa anti-SEZ6 site-specific antibody comprising a native kappa light chain (LC) constant region and a heavy chain (HC) constant region mutated to provide an unpaired cysteine. In this regard cysteine 220 (C220) in the upper hinge region of the HC was substituted with serine (C220S) to provide the hSEZ6-1.ss1 antibody. When assembled, the HC and LC form an antibody comprising two free cysteines at the c-terminal ends of the light chain constant regions (e.g., C214) that are suitable for conjugation to a therapeutic agent. Unless otherwise noted all numbering of constant region residues is in accordance with the EU numbering scheme as set forth in Kabat et al.

To generate the site-specific constructs a VH nucleic acid was cloned onto an expression vector containing a C220S mutated HC constant region. Resulting vectors encoding the mutant C220S HC were co-transfected in CHO-S cells with a vector encoding the selected light chain variable region operably associated with a wild-type IgG1 kappa LC and expressed using a mammalian transient expression system.

In addition to the C220S mutation to provide the free cysteines in the constant region, two additional modifications were made on the heavy chain. First, the C-terminal lysine was deleted in order to reduce heterogeneity in expression. Second, a conservative mutation was made in the heavy chain variable region to improve molecular stability and facilitate antibody production. More specifically, a conservative mutation was incorporated in the heavy chain CDR2 (as defined by Kabat) to eliminate a canonical glycosylation site. Glycosylation at this site could potentially impart heterogeneity in the expressed protein which may result in a reduction in binding affinity. Accordingly, a substitution of serine to asparagine at Kabat position 60 (S60N) was incorporated into the heavy chain to eliminate the glycosylation site. The resulting humanized antibody with these mutations was termed hSEZ6-1.ss1. As discussed in more detail below, substantial equivalency of hSEZ6-1.ss1 to the parental humanized antibody and murine source antibody was confirmed as to affinity.

The resulting genetic arrangement for the humanized variable regions of the mutated antibody are shown in Table 3B immediately below.

TABLE 3B

| mAb | Human VH | Human JH | FW changes | CDR Changes (VH) | human VK | Human JK | FW changes | CDR Changes (VK) |
| --- | --- | --- | --- | --- | --- | --- | --- | --- |
| SEZ6-1.ss1 | IGHV5-51 | JH4 | none | S60N | IGKV-L6 | JK4 | none | none |

The amino acid sequence of the full-length hSEZ6-1.ss1 site-specific antibody heavy chain is SEQ ID NO:3, having the variable region mutation site S60N and constant region mutation site C220S. The amino acid sequence of the heavy chain variable region is shown below as SEQ ID NO:7, having the S60N mutation underlined.

(SEQ ID NO: 7)
EVQLVQSGAEVKKPGESLKISCKGSGYSFTSSWINWVRQMPGKGLEWMG
RIYPGEGDTNY<u>N</u>GNFEGQVTISADKSISTAYLQWSSLKASDTAMYYCTR
GLVMDYWGQGTLVTVSS

The amino acid sequence of the full-length hSEZ6-1.ss1 site-specific antibody light chain is SEQ ID NO:4, having the toxin conjugation residue at C214. The amino acid sequence of the light chain variable region is shown below as SEQ ID NO:8

(SEQ ID NO: 8)
EIVLTQSPATLSLSPGERATLSCRASQSVDYNGISYMHVVYQQKPGQAP
RLLIYAASNVQSGIPARFSGSGSGTDFTLTISSLEPEDFAVYYCQQSIE
DPPTFGGGTKVEIK

Example 3: Preparation of hSEZ6-1.ss1 Drug Linker

A drug linker compound according to Formula II

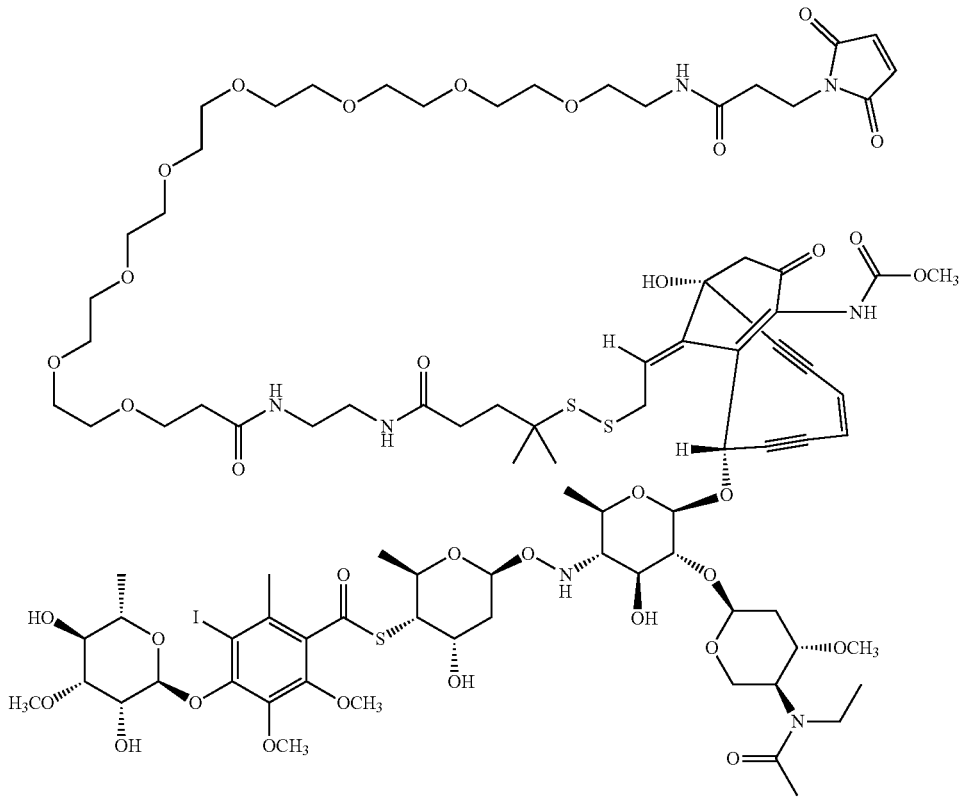

Formula II was synthesized as set forth immediately below.

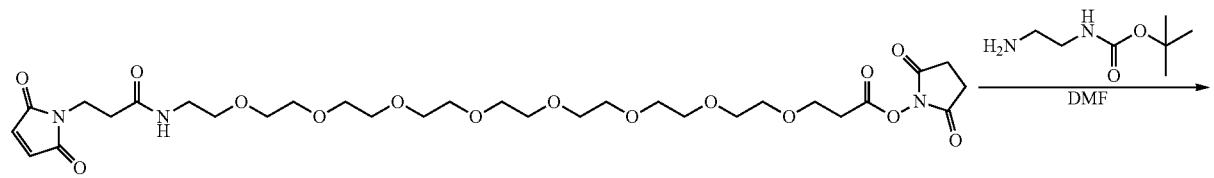

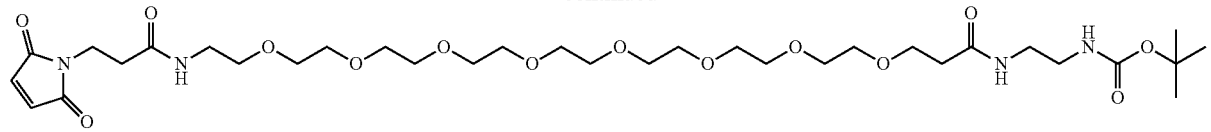

Step 1. tert-butyl [34-(2,5-dioxo-2,5-dihydro-1H-pyrrol-1-yl)-4,32-dioxo-7,10,13,16,19,22,25,28-octaoxa-3,31-diazatetratriacontan-1-yl]carbamate 3-(2,5-Dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacosan-1-yl}propanamide (434 mg) was dissolved in N,N-dimethylformamide (5 mL) and treated with tert-butyl (2-aminoethyl)carbamate (108.1 mg). After 6 hours the reaction mixture was concentrated, and the residue purified by silica gel chromatography eluted with 0% CH$_3$OH/CH$_2$Cl$_2$ to 10% CH$_3$OH/CH$_2$Cl$_2$ to give the titled compound (154.2 mg). LC/MS (Analytical method A): Rt=1.65 min, m/z 735.46 [M+H]$^+$.

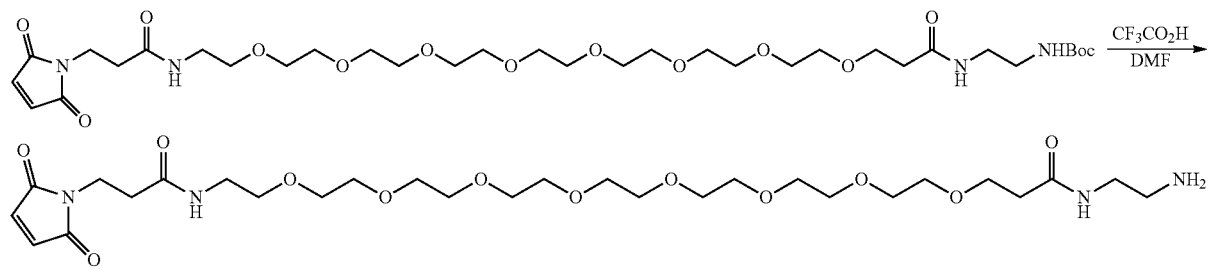

Step 2. N-(2-aminoethyl)-31-(2,5-dioxo-2,5-dihydro-1H-pyrrol-1-yl)-29-oxo-4,7,10,13,16,19,22,25-octaoxa-28-azahentriacontan-1-amide The tert-butoxycarbonyl protected amine (Step 1, 154.2 mg) was dissolved in N,N-dimethylformamide (5 mL), trifluoroacetic acid (500 μL) was added over 30 seconds, and the resultant mixture was stirred for 30 minutes. After reaction completion, the reaction mixture was concentrated and used without further purification. LC/MS (Analytical method A): Rt=1.29 min, m/z 635.39 [M+H]$^+$.

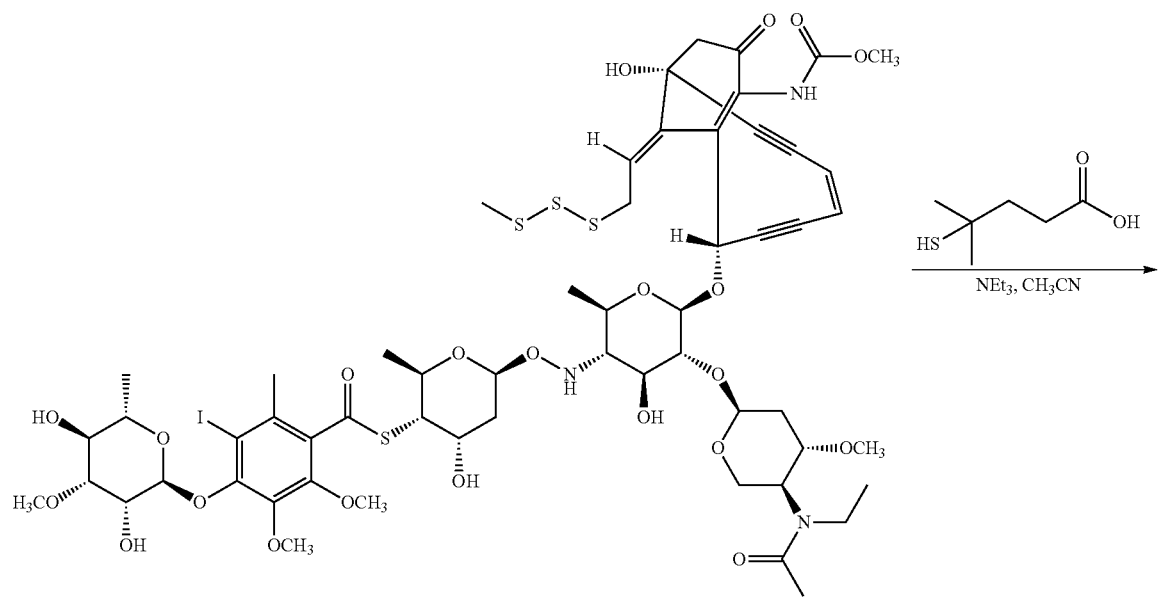

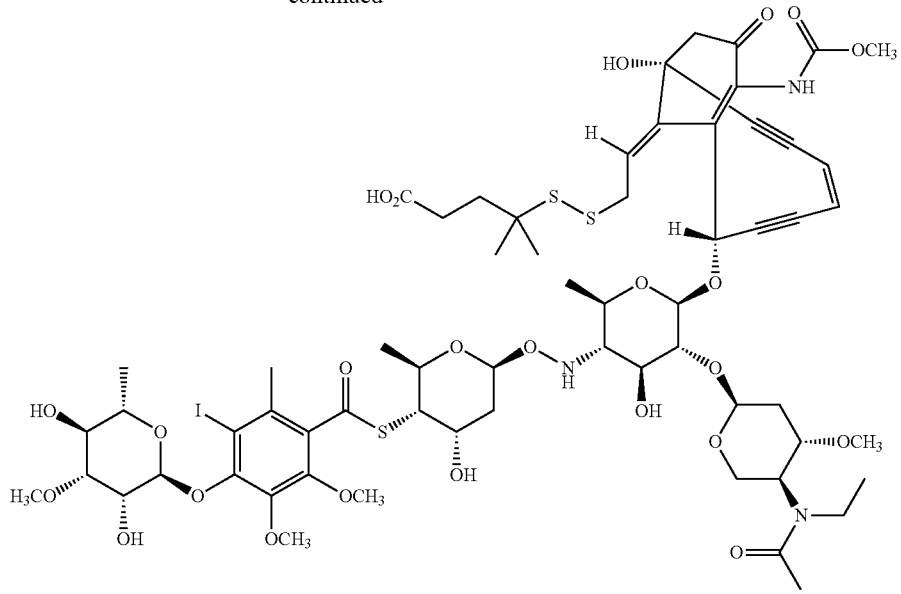

Step 3. 4-{[(2E)-2-{(1R,4Z,8S)-8-({(2R,3R,4S,5S,6R)-3-({(2S,4S,5S)-5-[acetyl(ethyl)amino]-4-methoxyoxan-2-yl}oxy)-5[({(2S,4S,5S,6R)-5-[(4-{[(2S,3R,4R,5S,6S)-3,5-dihydroxy-4-methoxy-6-methyloxan-2-yl]oxy}-3-iodo-5,6-dimethoxy-2-methylbenzoyl)sulfanyl]-4-hydroxy-6-methyloxan-2-yl}oxy)amino]-4-hydroxy-6-methyloxan-2-yl}oxy)-1-hydroxy-10-[(methoxycarbonyl)amino]-11-oxobicyclo[7.3.1]trideca-4,9-diene-2,6-diyn-13-ylidene}ethyl]disulfanyl}-4-methylpentanoic acid N-Acetyl calicheamicin γ 1 (0.2 g, 0.142 mmol, 1 eq) was dissolved in acetonitrile (30 mL), and the resultant solution was chilled to −15° C. 4-Mercapto-4-methylpentanoic acid (0.420 mL, 2.837 mmol, 20 eq) was dissolved in acetonitrile (10 mL) and added slowly to the cooled solution of N-acetyl calicheamicin γ1. Triethylamine (0.377 mL, 2.837 mmol, 20 eq) was added to the reaction mixture, and then the reaction mixture was allowed to warm up to room temperature over 3-18 hours. Upon completion of the reaction, the mixture was concentrated, and the residue was dry loaded onto silica gel for flash chromatography purification eluted with 2-20% methanol/dichloromethane to give the titled compound. The titled compound was precipitated out of cold diethyl ether. LC/MS (analytical method A): Rt=1.92 min, m/z 1478.64 [M+H]$^+$.

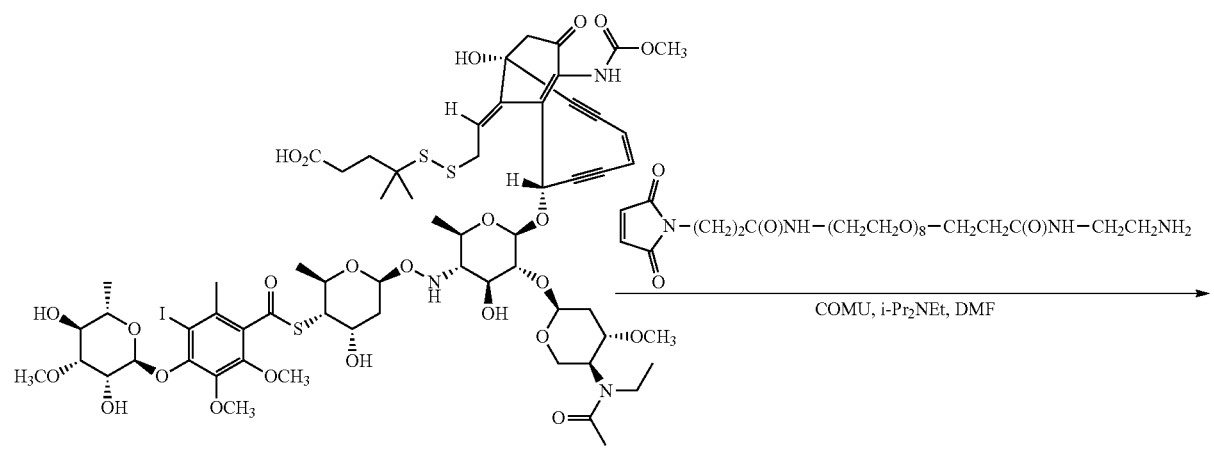

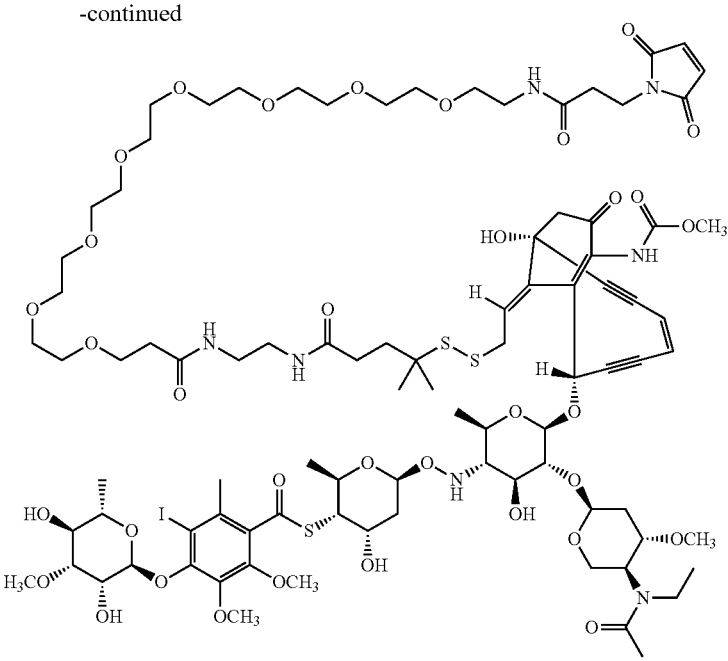

Step 4. S-[(2R,3S,4S,6S)-6-({[(2R,3S,4S,5R,6R)-5-({(2S,4S,5S)-5-[acetyl(ethyl)amino]-4-methoxyoxan-2-yl}oxy)-6-{[(2S,5Z,9R,13E)-13-[43-(2,5-dioxo-2,5-dihydro-1H-pyrrol-1-yl)-5,5-dimethyl-8,13,41-trioxo-16,19,22,25,28,31,34,37-octaoxa- 3,4-dithia-9,12,40-triazatritetracontan-1-ylidene]-9-hydroxy-12-[(methoxycarbonyl)amino]-11-oxobicyclo[7.3.1]trideca-1(12),5-diene-3,7-diyn-2-yl]oxy}-4-hydroxy-2-methyloxan-3-yl]amino}oxy)-4-hydroxy-2-methyloxan-3-yl]4-{[(2S,3R,4R,5S,6S)-3,5-dihydroxy-4-methoxy-6-methyloxan-2-yl]oxy}-3-iodo-5,6-dimethoxy-2-methylbenzene-1-carbothioate N-Acetyl calicheamicin acid (Step 3, 100 mg, 0.068 mmol, 1 eq) was dissolved in N,N-dimethylformamide (3.4 mL) and cooled to 0° C. N,N-Diisopropylethylamine (176 μL, 1.01 mmol, 15 eq) and (1-cyano-2-ethoxy-2-oxoethylidenaminooxy)dimethylamino-morpholino-carbenium hexafluorophosphate (COMU, 43 mg, 0.1 mmol, 1.5 eq) were then sequentially added. After 2 minutes, the N-(2-aminoethyl)-31-(2,5-dioxo-2,5-dihydro-1H-pyrrol-1-yl)-29-oxo-4,7,10,13,16,19,22,25-octaoxa-28-azahentriacontan-1-amide (Step 2, 51.4 mg, 0.08 mmol, 1.2 eq) in N,N-dimethylformamide (200 μL) was added. After 1 hour, the reaction mixture was concentrated, and the residue was purified by preparative HPLC (method pA) to give the titled compound (16.8 mg, 12% yield). LC/MS (Analytical method B or C): Rt=8.18 min. HRMS calculated [M+H]$^+$=2094.7049, Observed [M+H]$^+$=2094.6902. $^1$H NMR (400 MHz, DMSO-d$_6$) δ9.03 (s, 1H), 8.01 (t, J=5.5 Hz, 1H), 7.86 (s, 2H), 7.01 (s, 3H), 6.80 (d, J=8.0 Hz, 1H), 6.30-6.18 (m, 1H), 6.13 (dd, J=9.5, 7.1 Hz, 1H), 6.09-5.99 (m, 2H), 5.56 (d, J=4.0 Hz, 1H), 5.45 (s, 1H), 5.43-5.37 (m, 2H), 5.12 (dd, J=13.4, 5.1 Hz, 2H), 4.94 (d, J=9.9 Hz, 1H), 4.63-4.47 (m, 2H), 4.27-4.13 (m, 2H), 4.11 (s, 1H), 4.08-3.97 (m, 1H), 3.91 (dd, J=10.8, 6.1 Hz, 1H), 3.81 (s, 3H), 3.78-3.81 (m, 1H), 3.77 (s, 3H), 3.73-3.63 (m, 1H), 3.63-3.55 (m, 7H), 3.55-3.46 (m, 30H), 3.41 (s, 3H), 3.25 (d, J=2.3 Hz, 3H), 3.15 (q, J=5.8 Hz, 2H), 3.07 (s, 5H), 2.93 (d, J=17.7 Hz, 1H), 2.47-2.38 (m, 1H), 2.36-2.26 (m, 7H), 2.15-2.06 (m, 2H), 2.01 (d, J=2.7 Hz, 3H), 1.87 (d, J=12.3 Hz, 1H), 1.80-1.62 (m, 3H), 1.26 (dd, J=6.1, 3.3 Hz, 4H), 1.24-1.19 (m, 2H), 1.19-1.12 (m, 7H), 1.09 (t, J=7.1 Hz, 2H), 0.95 (t, J=6.9 Hz, 1H).

General Information on Analytical and Preparative HPLC Methods.

Analytical Method A:

MS: Waters® Acuity® Ultra SQ Detector ESI, Scan range 120-2040 Da.

Column: Waters Acuity UPLC® BEH C18, 1.7 μm, 2.1×50 mm

Column temperature: 50° C.

Flow rate: 0.6 mL/min

Mobile phase A: 0.1% formic acid in water.

Mobile phase B: 0.1% formic acid in acetonitrile.

Gradient:

| Time, minutes | % A | % B |
| --- | --- | --- |
| 0 | 95 | 5 |
| 0.25 | 95 | 5 |
| 2 | 0 | 100 |
| 2.5 | 0 | 100 |
| 3 | 95 | 5 |
| 4 | 95 | 5 |

Analytical method B:

MS: Waters® Acuity® Ultra SQ Detector ESI, Scan range 120-2040 Da,

Column: Waters Acuity UPLC® BEH C18, 1.7 μm, 2.1×50 mm

Column temperature: 60° C.

Flow rate: 0.4 mL/min

Mobile phase A: 0.1% formic acid in water.

Mobile phase B: 0.1% formic acid in acetonitrile.

Gradient:

| Time, minutes | % A | % B |
| --- | --- | --- |
| 0 | 95 | 5 |
| 2 | 95 | 5 |
| 3 | 80 | 20 |
| 13 | 20 | 80 |
| 14 | 20 | 80 |

| Time, minutes | % A | % B |
| --- | --- | --- |
| 14.10 | 5 | 95 |
| 15 | 5 | 95 |
| 15.10 | 95 | 5 |
| 20 | 95 | 5 |

Analytical method C:
HRMS: AB Sciex 5600 Plus Triple Time-of-Flight (TOF), scan range 250-2500 Da
Column: Waters Acuity UPLC® BEH C18, 1.7 μm, 2.1×50 mm
Column temperature: 60° C.
Flow rate: 0.4 mL/min
Mobile phase A: 0.1% formic acid in water.
Mobile phase B: 0.1% formic acid in acetonitrile.
Gradient:

| Time, minutes | % A | % B |
| --- | --- | --- |
| 0 | 95 | 5 |
| 2 | 95 | 5 |
| 3 | 80 | 20 |
| 13 | 20 | 80 |
| 14 | 20 | 80 |
| 14.10 | 5 | 95 |
| 15 | 5 | 95 |
| 15.10 | 95 | 5 |
| 20 | 95 | 5 |

Analytical method D
Column: EMD Millipore Chromolith® Flash RP-18 end-capped 25-2 mm.
Column temperature: 40° C.
Wavelength: 220 nm
Flow rate: 1.5 mL/minute
Mobile phase A: $H_2O$ (4 L with 1.5 mL trifluoroacetic acid)
Mobile phase B: acetonitrile (4 L with 0.75 mL trifluoroacetic acid)
Gradient:

| Time, minutes | % A | % B |
| --- | --- | --- |
| 0 | 95 | 5 |
| 0.01 | 95 | 5 |
| 0.70 | 5 | 95 |
| 1.15 | 5 | 95 |
| 1.16 | 95 | 5 |
| 1.60 | 95 | 5 |

Analytical method E
Column: Halo C18 2.1×30 mm, 2.7 μm
Detection: diode array and positive/negative electrospray ionization
Flow rate: 1.0 mL/minute
Mobile phase A: 0.0375% trifluoroacetic acid in water
Mobile phase B: 0.018% trifluoroacetic acid in acetonitrile
Gradient:

| Time, minutes | % A | % B |
| --- | --- | --- |
| 0 | 90 | 10 |
| 2.00 | 20 | 80 |
| 2.48 | 20 | 80 |
| 2.50 | 90 | 10 |
| 3.00 | 90 | 10 |

Analytical method F
Column: Venusil XBP-C18, 2.1×50 mm, 5 μm
Detection: diode array and positive/negative electrospray ionization
Flow rate: 0.8 mL/minute
Mobile phase A: 0.0375% trifluoroacetic acid in water
Mobile phase B: 0.018% trifluoroacetic acid in acetonitrile
Gradient:

| Time, minutes | % A | % B |
| --- | --- | --- |
| 0 | 99 | 1 |
| 3.40 | 10 | 90 |
| 3.85 | 0 | 100 |
| 3.86 | 99 | 1 |
| 4.51 | 99 | 1 |

Preparative HPLC Method pA:
Column: Waters XBridge™ prep C18 5 μm OBD, 19×100 mm
Column temperature: ambient
Flow rate: 15 mL/min
Mobile phase A: 0.1% formic acid in water.
Mobile phase B: 0.1% formic acid in acetonitrile.
Gradient:

| Time, min | % A | % B |
| --- | --- | --- |
| 0 | 95 | 5 |
| 5 | 95 | 5 |
| 8 | 80 | 20 |
| 50 | 20 | 80 |
| 52.59 | 20 | 80 |
| 52.92 | 5 | 95 |
| 55.87 | 5 | 95 |
| 56.20 | 95 | 5 |
| 60 | 95 | 5 |

Preparative HPLC method pB:
Column: Phenomenex Luna® C18(2), 250×50 mm i.d., 10 μm
Wavelengths: 220 and 254 nm
Flow rate: 80 mL/minute
Mobile phase A: 0.01 M $NH_4HCO_3$ in $H_2O$.
Mobile phase B: acetonitrile
Gradient: 30-50% mobile phase B over 20 minutes
Preparative HPLC Method pC
Column: Phenomenex Luna® C18(2), 250×50 mm i.d., 10 μm
Wavelengths: 220 and 254 nm
Flow rate: 80 mL/minute
Mobile phase A: 0.075% v/v trifluoroacetic acid in water
Mobile phase B: acetonitrile
Gradient: 10-40% mobile phase B over 20 minutes
Preparative HLC Method pD
Column: Phenomenex Luna® C18(2), 250×50 mm i.d., 10 μm Wavelengths: 220 and 254 nm
Flow rate: 80 mL/minute
Mobile phase A: 0.09% v/v trifluoroacetic acid in water
Mobile phase B: acetonitrile
Gradient: 15-43% mobile phase B over 20 minutes Example 4: Preparation of hSEZ6-1.ss1 Antibody Drug Conjugates Anti-hSEZ6-1.ss1 ADCs were prepared according to the teachings herein for further in vitro and in vivo testing.

In this regard hSEZ6-1.ss1 from Example 2 was conjugated to a non-cleavable calicheamicin drug linker (Formula II prepared as in Example 3) via a terminal maleimido moiety with a free sulfhydryl group to create the disclosed SEZ6 ADC which is termed hSEZ6-1.ss1 ADC1 herein. In addition, three control SEZ6 ADCs were fabricated by conjugating hSEZ6-1.ss1 to the same calicheamicin payloads but comprising cleavable linkers (ADC2, ADC3 and ADC4). Finally, the control ADCs were made comprising hSEZ6-1.ss1 without the S60N mutation.

The site-specific humanized SEZ6 ADC (hSEZ6-1.ss1) was conjugated using a modified partial reduction process. The desired product is an ADC that is maximally conjugated on the unpaired cysteine (C214) on each LC constant region and that minimizes ADCs having a drug loading which is greater than 2 while maximizing ADCs having a drug loading of 2. In order to further improve the specificity of the conjugation, the antibodies were selectively reduced using a process comprising a stabilizing agent (e.g. L-arginine) and a mild reducing agent (e.g. glutathione) prior to conjugation with the linker drug, followed by a diafiltration and formulation step.

More specifically a preparation of each antibody was partially reduced in a buffer containing 1M L-arginine/5 mM EDTA with a pre-determined concentration of reduced glutathione (GSH), pH 8.0 for a minimum of 20 hours at room temperature. All preparations were then buffer exchanged into a 20 mM Tris/3.2 mM EDTA, pH 7.0 buffer using a 30 kDa membrane (Millipore Amicon Ultra) to remove the reducing buffer. The resulting partially reduced preparations were then conjugated to the respective calicheamicin drug linker via a maleimide group for a minimum of 60 mins. at room temperature. The pH was then adjusted to 6.0 with the addition of 0.5 M acetic acid. Preparations of the ADCs were buffer exchanged into diafiltration buffer by diafiltration using a 30 kDa membrane. The dialfiltered SEZ6 ADC was then formulated with sucrose and polysorbate-20 to the target final concentration.

The resulting formulation was then analyzed for protein concentration (by measuring UV), aggregation (SEC), drug to antibody ratio (DAR) by reverse-phase HPLC (RP-HPLC) and activity (in vitro cytotoxicity). It was then frozen and stored until use.

A schematic representation of hSEZ6-1.ss1 ADC1 is presented in FIG. 1 appended hereto.

Example 5: In Vitro Characteristics of hSEZ6-1.Ss1 Antibody

Experiments were run to test whether the S60N mutation affected the interaction between the hSEZ6-1.ss1 mAb and the SEZ6 antigen. In this regard the binding of soluble SEZ6-his antigen to surface-immobilized SEZ6 antibodies and SEZ6 ADCs, with and without the S60N mutation, were measured on a Biacore T200 (anti-human capture chip).

More specifically 5 µg/mL IgG were flowed for 12 sec at 5 µL/min, yielding 115-124 RU immobilization response. 22, 66 and 200 nM hSEZ6-his was injected for 90 sec at 30 µL/min, followed by 300 sec dissociation. Surfaces were regenerated by flowing 2M Magnesium Chloride (30 µL/min, 30 sec) at the end of each cycle. Sensorgrams were double referenced (buffer injection and control flow cell) and are set forth in FIG. 2 where the antibody with the mutation is labeled hSEZ6-1.ss1 and the source antibody, without the mutation, is labeled hSEZ6-1.ss1 parent.

Additionally, affinity measurements were made using a Biacore T200 to determine the binding characteristics of hSEZ6-1.ss1 comprising S60N. In this regard Fab constructs of the hSEZ6-1.ss1 antibody, with and without the S60N mutation, were fabricated and purified. The binding of the Fab constructs to soluble surface immobilized human SEZ6-His ligand was then compared on a Biacore T200 (anti-His capture chip). More specifically of 2 μg/mL human SEZ6-His were flowed across the chip for 12 sec at 5 μL/min, yielding 45-66 RU immobilization response. 22, 66 and 200 nM injections of Fab occurred for 90 sec at 30 μL/min, followed by 400-450 second dissociation. Surfaces were regenerated by flowing 10 mM Glycine, pH 1.5 for 60 seconds at 30 uL/min. Sensorgrams were double referenced (buffer injection and control flow cell). The results are shown in Table 4 immediately below.

TABLE 4

| Analyte | ka (1/Ms) | kd (1/s) | hSEZ6-His KD (nM) | Rmax (RU) |
|---|---|---|---|---|
| Wild Type Fab | 1.1E+06 | 0.006 | 5.8 | 35.2 |
| MutA (S60N) Fab | 1.3E+06 | 0.006 | 4.8 | 4.0 |

A review of FIG. 2 shows that the S60N mutation and removal of the glycosylation site in the heavy chain variable region does not materially alter the binding properties of hSEZ6-1.ss1 antibodies when compared with the parent antibody lacking the mutation. Similarly, the affinity measurements shown in Table 4 demonstrate that the introduced mutation does not adversely impact the binding of the antibody used in the disclosed ADC. As such, the potentially destabilizing position may be modified without compromising the pharmaceutical effectiveness of the molecule.

Example 6: hSEZ6 ADCs Effectively Kill hSEZ6 Expressing Cells In Vitro

To determine whether anti-SEZ6 ADCs of the invention can efficiently mediate the delivery of conjugated cytotoxic agents to live cells, an in vitro cell killing assay was performed using the anti-SEZ6 ADCs produced in Example 4 above.

Single cell suspensions of HEK293T cells overexpressing hSEZ6 or naïve HEK293T cells were plated at 500 cells per well into BD Tissue Culture plates (BD Biosciences). One day later, various concentrations of purified ADC conjugated to calicheamicin were added to the cultures. The cells were incubated for 96 hours. After the incubation viable cells were enumerated using CellTiter-Glo® (Promega) as per the manufacturer's instructions. Raw luminescence counts using cultures containing non-treated cells were set as 100% reference values and all other counts were calculated as a percentage of the reference value.

FIG. 3 shows that all hSEZ6 expressing cells treated were much more sensitive to the anti-SEZ6 ADCs as compared to the naïve HET293T cells, demonstrating the specificity of the ADCs to the SEZ6 antigen.

The above results demonstrate the ability of anti-SEZ6 ADCs to specifically mediate internalization and delivery of directly conjugated cytotoxic payloads to cells expressing SEZ6.

Example 7: ADC Pharmacokinetics in Immunocompromised Mice

Pharmacokinetics (PK) of hSEZ6-1.ss1 ADC1, hSEZ6-1.ss1 ADC2, and hSEZ6-1.ss1 ADC3 were evaluated in NOD SCID mice. Mice (n=4 females per group) were randomized into treatment groups having equal average body weight, and then treated with the same amount of ADCs via a single intravenous injection (100 µL volume). The ADCs were each co-administered with 10 mg/kg unconjugated HuIgG1 antibody in order to saturate the FcγR-mediated clearance and provide suitable ADC exposure. Serum samples were collected at 5 min, 4, 24, 72, 120, 168, 216, and 336 hours after each dose, and total antibody (TAb) and ADC concentrations were assessed by MSD immunoassay. Pharmacokinetics parameters including maximum concentrations (Cmax), exposure (area under the curve or AUC) evaluated from time=0 to 14 days post-dosing) and half-life, were evaluated using non-compartmental analysis methods.

ADC and TAb serum pharmacokinetics declined bi-exponentially for all the ADCs and peak concentrations (Cmax) were observed at 5 minutes post dose. There was no significant difference in ADC exposure (AUC 0-14 Days) between the tested SEZ6 ADCs. ADC serum terminal half-life was similar between the ADCs. ADC stability was measured by the ratio of TAb to ADC exposures, and was similar for the tested compounds, ranging from 1.4 to 1.6. Taken together, these data demonstrate that the pharmacokinetics of hSEZ6-1.ss1 ADC1, hSEZ6-1.ss1 ADC2, and hSEZ6-1.ss1 ADC3 are comparable in NOD SCID mice.

Example 8: hSEZ6-1.ss1 Antibody Drug Conjugates Suppress Tumor Growth In Vivo

In vivo experiments were conducted to confirm the cell killing ability of the hSEZ6-1.ss1 ADC1, hSEZ6-1.ss1 ADC2, and hSEZ6-1.ss1 ADC3 demonstrated in Example 6. To this end, site-specific SEZ6-targeted ADCs prepared as set forth in the previous Examples were tested for in vivo therapeutic effects in immunocompromised NOD SCID mice bearing subcutaneous patient-derived xenograft (PDX) small cell lung cancer (SCLC) tumors having endogenous SEZ6 cell surface protein expression. Anti-SEZ6 conjugates hSEZ6-1.ss1 ADC1, hSEZ6-1.ss1 ADC2, and hSEZ6-1.ss1 ADC3 were each tested in two different SCLC models.

SCLC-PDX lines, LU95 and LU149 were each injected as a dissociated cell inoculum under the skin near the mammary fat pad region and measured weekly with calipers (ellipsoid volume=a×b$^2$/2, where a is the long diameter, and b is the short diameter of an ellipse). After tumors grew to an average size of 130-200 mm$^3$ (range, 100-300 mm$^3$) the mice were randomized into treatment groups (n=5 mice per group) of equal tumor volume averages. Mice (5 per group) were treated with identical single doses of either vehicle (5% glucose in sterile water), or HuIgG1- or SEZ6-ADC preparations via an intraperitoneal injection (100 µL volume). SEZ6-ADC was co-administered with 10 mg/kg naked, HuIgG1 antibody in order to linearize the pharmacokinetics.

Therapeutic effects assessed by weekly tumor volume (with calipers as above) and weight measurements. Endpoint criteria for individual mice or treatment groups included health assessment (any sign of sickness), weight loss (more than 20% weight loss from study start), and tumor burden (tumor volumes >1000 mm$^3$). Efficacy was monitored by weekly tumor volume measurements (mm$^3$) until groups reached an average of approximately 800-1000 mm$^3$. Tumor volumes were calculated as an average with standard error of the mean for all mice in treatment group and were plotted versus time (days) since initial treatment. The results of the treatments are depicted in FIGS. 4A and 4B where mean tumor volumes with standard error of the mean (SEM) in 5 mice per treatment group are shown.

SEZ6-binding ADCs conjugated to calicheamicin (hSEZ6-1.ss1 ADC1, hSEZ6-1.ss1 ADC2, and hSEZ6-1.ss1 ADC3) were evaluated in mice bearing SCLC PDX-LU95 (FIG. 4A) or PDX-LU149 (FIG. 4B). Non-cleavable linker ADC1 had similar or greater efficacy compared to cleavable linker ADC2 while cleavable linker ADC3 had greater efficacy compared to ADC1 at 2 mg/kg. In any event, hSEZ6-1.ss1 ADC1 and hSEZ6-1.ss1 ADC3 can achieve durable responses for 50 days or longer in SCLC PDX. The response was SEZ6-ADC specific, as there was no response observed following treatment with non-binding ADCs (HuIgG1) conjugated to the same calicheamicin drug linkers (data not shown).

Such results demonstrate that hSEZ6-1.ss1 ADC1, fabricated as set forth herein, has the potential to be pharmaceutically effective in retarding the growth of small cell lung cancer cells.

Example 9: hSEZ6-1.ss1 ADC1 Exhibits a Robust Safety Margin

An analysis was conducted to determine the safety margin provided by hSEZ6-1.ss1 ADC1.

In this regard hSEZ6-1.ss1 ADC1, hSEZ6-1.ss1 ADC2 and hSEZ6-1.ss1 ADC3 comprise an identical targeted mAb (hSEZ6-1.ss1) and warhead (N-acetyl gamma calicheamicin), with differences in the linker drug attachment. hSEZ6-1.ss1 ADC1 is unique in that it comprises a non-cleavable linker as compared to the other cathepsin B-susceptible di-peptide based linker drugs. The SEZ6 ADCs were evaluated in four discrete high-expressing SEZ6 SCLC mouse PDX models (LU64, LU86, LU95 and LU149), and in an exploratory repeat-dose toxicity study in cynomolgus monkeys.

A semi-mechanistic PK/PD model based on untreated tumor growth and SEZ6 ADC-treated tumor response data in mouse was used to predict the tumor-static concentrations (TSC) that correspond to an ADC concentration resulting in tumor stasis in patients. Subsequently, human PK was simulated based on cynomolgus monkey PK data. Predictions of human PK were then used to estimate the dose required to achieve a plasma trough concentration at the dose interval in patients that is equivalent to the TSC. Safety margins were estimated by comparing the ADC exposures at the maximum tolerated dose (MTD) in cynomolgus monkey with the exposure at the predicted human efficacious dose. This analysis was repeated for each lung PDX models evaluated (LU64, LU86, LU95 and LU149).

Table 5 provides the predicted safety margin for each of the SEZ6 ADCs. Based on this analysis, hSEZ6-1.ss1 ADC1 was predicted to be more tolerable than the other SEZ6 ADCs (hSEZ6-1.ss1 ADC2, hSEZ6-1.ss1 ADC3) conjugated to the same payload but with cleavable linkers. This analysis predicted a safety margin of approximately 10 for hSEZ6-1.ss1 ADC1 which is considerably higher than the two constructs with cleavable linkers.

TABLE 5

| Compound | Estimated Safety Margin |
| --- | --- |
| hSEZ6-1.ss1 ADC1 | 10 |
| hSEZ6-1.ss1 ADC2 | 0.3 |
| hSEZ6-1.ss1 ADC3 | 5.5 |

The predicted higher safety margin in humans based on data obtained in cynomolgus monkeys, and corresponding dosing flexibility indicates that hSEZ6-1.ss1 ADC1 is a strong therapeutic candidate.

Example 10: hSEZ6-1.ss1 ADC1 is Particularly Active in SCLC

To further demonstrate the potential efficacy of the disclosed ADC, toxin specific assays were conducted using various tumor xenograft cell lines. Initially SCLC, BR, CR, GA, NSCLC and PA PDX cell lines were interrogated via microarray analysis to determine the respective expression level of SEZ6 antigen (FIG. 5A) and CD46, a known positive control antigen (FIG. 5B). The microarray analysis was conducted using the Affymetrix ClariomD assay on purified RNA samples derived from human PDX. A review of FIGS. 5A and 5B shows that, while SEZ6 expression is upregulated in SCLC tumors compared to other tumor types, the positive antigen control CD46 exhibited consistently high mRNA expression levels across the panel of patient derived xenografts (PDX). Accordingly, the CD46 antigen was used as a surrogate ADC target to gauge the impact of the disclosed novel calicheamicin drug linker (Formula II) on various tumor types.

In this respect N149, a humanized CD46 antibody (U.S. Pat. No. 10,017,565 B2) was conjugated to the calicheamicin drug linker set forth herein or to a pyrrolobenzodiazepine (PBD) drug linker control. The ADCs were generated substantially as set forth in Example 4 above. Following preparation, the CD46 ADCs were frozen and stored until use.

PDX cells were inoculated into the flank of NOD-SCID mice. When tumors reached between 100-300 mm3, PBD ADC preparations were introduced as a single 1.6 mg/kg dose (FIG. 5C) while the calicheamicin ADC preparations were administered as a single 8 mg/kg dose for all tumor types other than the SCLC PDX (FIG. 5D). For the SCLC PDX the calicheamicin ADC preparation was administered as a 2 mg/kg or a 4 mg/kg dose (FIG. 5D). The tumors were then monitored for changes compared to non-targeting ADC preparation with the same warhead. Delta Time to Tumor progression (dTTP) were calculated by subtracting the progression time for nontargeting ADC from the progression time for targeting agent. Tumor progression was defined as the time pint where the observed measurement regrows at least 100 mm$^3$ greater than the nadir volume post-treatment. Each data point in FIGS. 5C and 5D represents an individual PDX cell line of the respective tumor type.

As shown in FIG. 5C the PBD ADC preparations provided a relatively uniform tumor response regardless of the PDX tumor type. In particular, susceptibility of the SCLC PDX to killing by the PBD toxin was largely equivalent to that of the other tumor cell lines. In sharp contrast the SCLC PDX cell lines proved far more susceptible to killing by the calicheamicin ADCs than the other PDX cell lines (FIG. 5D). More specifically, after a single, 8 mg/kg dose of the calicheamicin ADC the majority of patient derived xenografts from BR, CR, GA and NSCLC tumors exhibited minimal to no response. There was a mixture of responses in pancreatic tumors but even the pancreatic tumors showed minimal responses (<25 days dTTP) in the majority of cell lines tested. Conversely, the lower 2 mg/kg (black circles) or 4 mg/kg (white circles) doses of the calicheamicin ADC consistently reduced SCLC tumor growth substantially more than higher doses of the calicheamicin ADC achieved on other PDX tumors. Moreover, the majority of the SCLC tumors exhibited growth delays of greater than 40 days as compared to a nontargeting antibody carrying the same warhead (data not shown).

These data suggest that SCLC tumors are more sensitive to a calicheamicin warhead than other DNA damaging warheads. This result was unexpected, as the expectation was that the calicheamicin warhead would provide similar results to those observed with the PBD warhead.

Embodiments

1. An isolated antibody that specifically binds human SEZ6 wherein the antibody comprises a heavy chain sequence of SEQ ID NO:3 and a light chain sequence of SEQ ID NO:4.

2. The antibody of embodiment 1 wherein the antibody is conjugated to a calicheamicin payload.

3. The antibody of embodiment 2 wherein the calicheamicin payload comprises N-Ac calicheamicin.

4. The antibody of embodiment 3 wherein the calicheamicin payload comprises Formula II.

5. A method of treating small cell lung cancer comprising administering an antibody of any one of embodiments 1-4 to a subject in need thereof.

6. A kit comprising one or more containers containing an antibody of any one of embodiments 1-4.

7. The kit of embodiment 6 further comprising a label or package insert associated with the one or more containers indicating that the antibody is for treating a subject having small cell lung cancer.

8. A pharmaceutical composition comprising an antibody of any one of embodiments 1-4.

9. A kit comprising one or more containers containing a pharmaceutical composition of embodiment 8.

10. The kit of embodiment 9 further comprising a label or package insert associated with the one or more containers indicating that the pharmaceutical composition is for treating a subject having small cell lung cancer.

11. A nucleic acid encoding all or part of an antibody of any one of embodiments 1-4.

12. A vector comprising the nucleic acid of embodiment 11.

13. A host cell comprising the nucleic acid of claim 11 or the vector of embodiments 12.

14. A SEZ6 ADC of the structure:

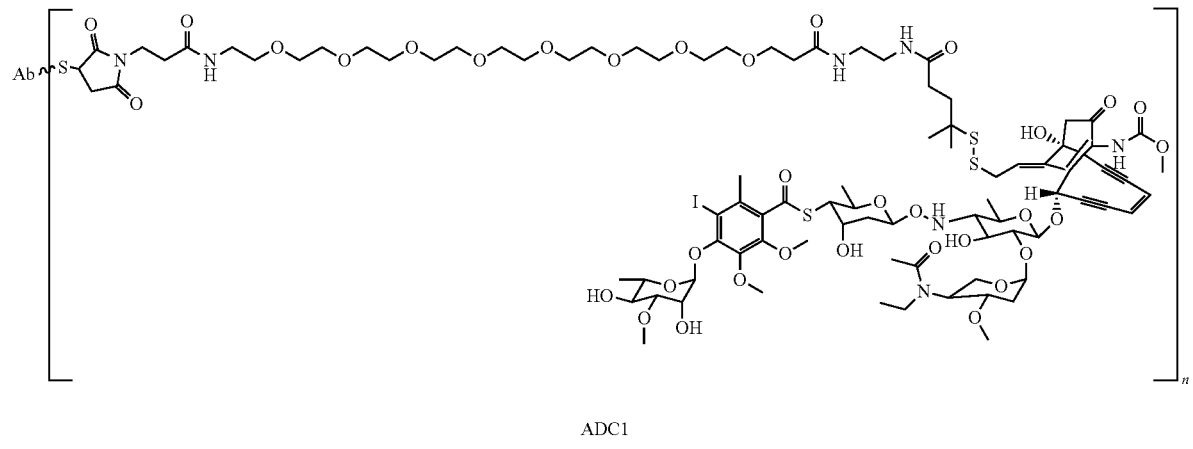

ADC1 wherein Ab comprises an anti-SEZ6 antibody having a heavy chain sequence of SEQ ID NO:3 and a light chain sequence of SEQ ID NO:4 and wherein n is 2.

15. A method of treating small cell lung cancer comprising administering a SEZ6 ADC of embodiment 14 to a subject in need thereof.

16. A kit comprising one or more containers containing the SEZ6 ADC of embodiment 14.

17. The kit of embodiment 16 further comprising a label or package insert associated with the one or more containers indicating that the SEZ6 ADC is for treating a subject having small cell lung cancer.

18. A pharmaceutical composition comprising the SEZ6 ADC of embodiment 14.

19. The pharmaceutical composition of embodiment 18 wherein the SEZ6 ADC of claim 14 is the predominant ADC species.

20. The pharmaceutical composition of embodiment 19 wherein the predominant ADC species comprises greater than about 70% of the ADC species present in the composition.

21. The pharmaceutical composition of embodiment 19 wherein the predominant ADC species comprises greater than about 80% of the ADC species present in the composition.

22. The pharmaceutical composition of embodiment 19 wherein the predominant ADC species comprises greater than about 90% of the ADC species present in the composition.

23. A kit comprising one or more containers containing any one of the pharmaceutical compositions of embodiments 18-22.

24. The kit of embodiment 23 further comprising a label or package insert associated with the one or more containers indicating that the pharmaceutical composition is for treating a subject having small cell lung cancer.

25. A method of treating small cell lung cancer comprising administering any one of the pharmaceutical compositions of embodiments 18-22.

26. A method of reducing tumor initiating cells in a tumor cell population, wherein the method comprises contacting a tumor cell population comprising tumor initiating cells and tumor cells other than tumor initiating cells, with a SEZ6 ADC of embodiment 14 whereby the frequency of tumor initiating cells is reduced.

27. The method of embodiment 26, wherein the contacting is performed in vivo.

28. The method of embodiment 26, wherein the contacting is performed in vitro.

29. A method of delivering a cytotoxin to a cell comprising contacting the cell with a SEZ6 ADC of embodiment 14.

30. A method of producing an ADC of embodiment 14 comprising the step of conjugating a hSEZ6-1.ss1 antibody having a heavy chain sequence of SEQ ID NO:3 and a light chain sequence of SEQ ID NO:4 with a drug linker comprising Formula II.

31. The method of embodiment 30 further comprising the step of lyophilizing the ADC.

32. A method of treating small cell lung cancer in a subject in need thereof comprising administering a SEZ6 ADC having a safety margin greater than 6 wherein the SEZ6 ADC comprises the structure:

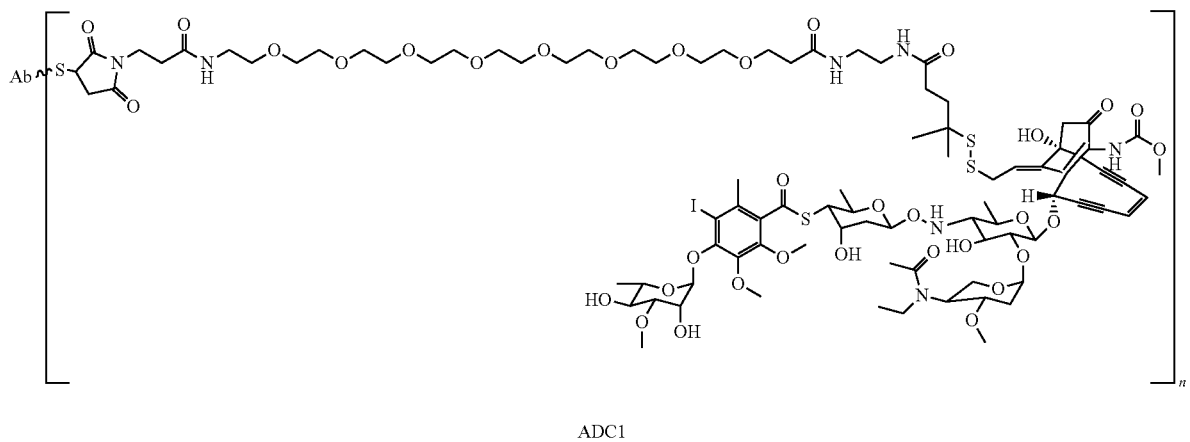

ADC1 wherein Ab comprises an anti-SEZ6 antibody having a heavy chain sequence of SEQ ID NO:3 and a light chain sequence of SEQ ID NO:4 and wherein n is 2.

33. The method of embodiment 32 wherein the safety margin is about 10.

34. A calicheamicin drug linker, or a pharmaceutically acceptable salt or solvate thereof, comprising the structure:

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, Formula II

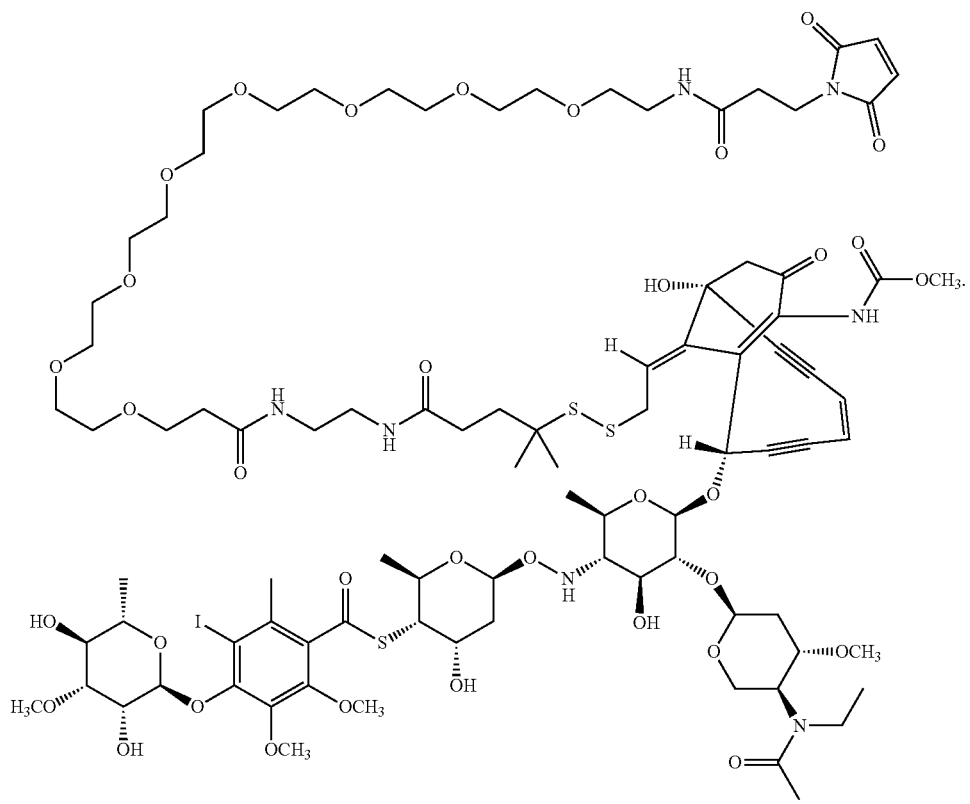

the present invention is not limited to the particular embodiments that have been described in detail herein. Rather, reference should be made to the appended claims as indicative of the scope and content of the invention.

---

What is claimed is:

1. An anti-human SEZ6 antibody, comprising a heavy chain sequence of SEQ ID NO:3 and a light chain sequence of SEQ ID NO:4.

2. The antibody of claim 1 wherein the antibody is conjugated to a calicheamicin payload.

3. The antibody of claim 2 wherein the calicheamicin payload comprises N-Ac calicheamicin.

4. A SEZ6 antibody drug conjugate (ADC) having the structure of ADC1:

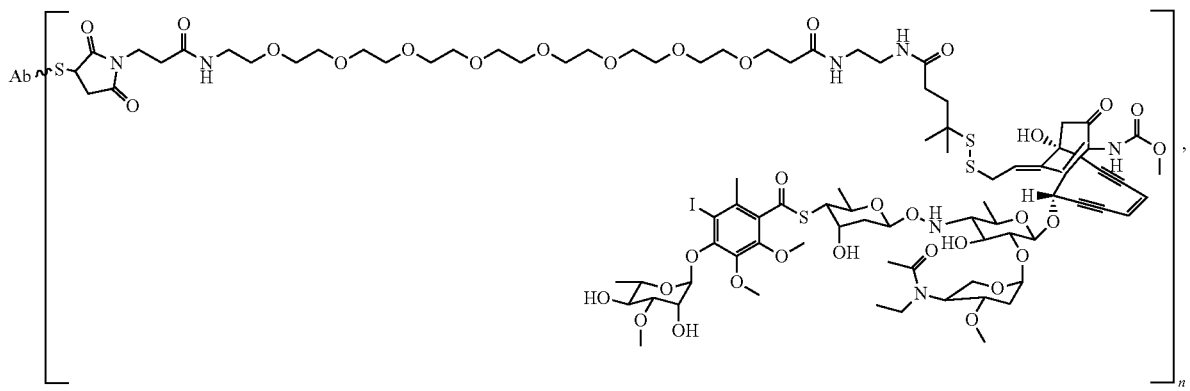

(ADC1)

wherein Ab comprises an anti-human SEZ6 antibody having a heavy chain sequence of SEQ ID NO:3 and a light chain sequence of SEQ ID NO:4, and n is 2.

* * * * *

UNITED STATES PATENT AND TRADEMARK OFFICE
CERTIFICATE OF CORRECTION

PATENT NO. : 11,077,203 B2
APPLICATION NO. : 16/908645
DATED : August 3, 2021
INVENTOR(S) : David Liu et al.

Page 1 of 1

It is certified that error appears in the above-identified patent and that said Letters Patent is hereby corrected as shown below:

In the Specification

Column 8, (SEQ ID: 4) Line 28:
EIVLTQSPATLSLSPGERATLSCRASQSVDYNGISYMHWYQQKPGQAPR Signed and Sealed this
Fourth Day of October, 2022

Katherine Kelly Vidal
*Director of the United States Patent and Trademark Office*

SEQUENCE LISTING

<160> NUMBER OF SEQ ID NOS: 8

<210> SEQ ID NO 1
<211> LENGTH: 994
<212> TYPE: PRT
<213> ORGANISM: Homo sapiens

<400> SEQUENCE: 1

```
Met Arg Pro Val Ala Leu Leu Leu Pro Ser Leu Leu Ala Leu Leu
1               5                   10                  15

Ala His Gly Leu Ser Leu Glu Ala Pro Thr Val Gly Lys Gly Gln Ala
            20                  25                  30

Pro Gly Ile Glu Glu Thr Asp Gly Glu Leu Thr Ala Ala Pro Thr Pro
            35                  40                  45

Glu Gln Pro Glu Arg Gly Val His Phe Val Thr Thr Ala Pro Thr Leu
50                  55                  60

Lys Leu Leu Asn His His Pro Leu Leu Glu Glu Phe Leu Gln Glu Gly
65                  70                  75                  80

Leu Glu Lys Gly Asp Glu Glu Leu Arg Pro Ala Leu Pro Phe Gln Pro
                85                  90                  95

Asp Pro Pro Ala Pro Phe Thr Pro Ser Pro Leu Pro Arg Leu Ala Asn
                100                 105                 110

Gln Asp Ser Arg Pro Val Phe Thr Ser Pro Thr Pro Ala Met Ala Ala
                115                 120                 125

Val Pro Thr Gln Pro Gln Ser Lys Glu Gly Pro Trp Ser Pro Glu Ser
        130                 135                 140

Glu Ser Pro Met Leu Arg Ile Thr Ala Pro Leu Pro Pro Gly Pro Ser
145                 150                 155                 160

Met Ala Val Pro Thr Leu Gly Pro Gly Glu Ile Ala Ser Thr Thr Pro
                165                 170                 175

Pro Ser Arg Ala Trp Thr Pro Thr Gln Glu Gly Pro Gly Asp Met Gly
                180                 185                 190

Arg Pro Trp Val Ala Glu Val Val Ser Gln Gly Ala Gly Ile Gly Ile
            195                 200                 205

Gln Gly Thr Ile Thr Ser Ser Thr Ala Ser Gly Asp Asp Glu Glu Thr
        210                 215                 220

Thr Thr Thr Thr Thr Ile Ile Thr Thr Thr Ile Thr Thr Val Gln Thr
225                 230                 235                 240

Pro Gly Pro Cys Ser Trp Asn Phe Ser Gly Pro Glu Gly Ser Leu Asp
                245                 250                 255

Ser Pro Thr Asp Leu Ser Ser Pro Thr Asp Val Gly Leu Asp Cys Phe
                260                 265                 270

Phe Tyr Ile Ser Val Tyr Pro Gly Tyr Gly Val Glu Ile Lys Val Gln
            275                 280                 285

Asn Ile Ser Leu Arg Glu Gly Glu Thr Val Thr Val Glu Gly Leu Gly
        290                 295                 300

Gly Pro Asp Pro Leu Pro Leu Ala Asn Gln Ser Phe Leu Leu Arg Gly
305                 310                 315                 320

Gln Val Ile Arg Ser Pro Thr His Gln Ala Ala Leu Arg Phe Gln Ser
                325                 330                 335

Leu Pro Pro Pro Ala Gly Pro Gly Thr Phe His Phe His Tyr Gln Ala
                340                 345                 350
```

```
Tyr Leu Leu Ser Cys His Phe Pro Arg Arg Pro Ala Tyr Gly Asp Val
            355                 360                 365

Thr Val Thr Ser Leu His Pro Gly Gly Ser Ala Arg Phe His Cys Ala
    370                 375                 380

Thr Gly Tyr Gln Leu Lys Gly Ala Arg His Leu Thr Cys Leu Asn Ala
385                 390                 395                 400

Thr Gln Pro Phe Trp Asp Ser Lys Glu Pro Val Cys Ile Ala Ala Cys
                405                 410                 415

Gly Gly Val Ile Arg Asn Ala Thr Thr Gly Arg Ile Val Ser Pro Gly
            420                 425                 430

Phe Pro Gly Asn Tyr Ser Asn Asn Leu Thr Cys His Trp Leu Leu Glu
            435                 440                 445

Ala Pro Glu Gly Gln Arg Leu His Leu His Phe Glu Lys Val Ser Leu
    450                 455                 460

Ala Glu Asp Asp Arg Leu Ile Ile Arg Asn Gly Asp Asn Val Glu
465                 470                 475                 480

Ala Pro Pro Val Tyr Asp Ser Tyr Glu Val Glu Tyr Leu Pro Ile Glu
                485                 490                 495

Gly Leu Leu Ser Ser Gly Lys His Phe Phe Val Glu Leu Ser Thr Asp
            500                 505                 510

Ser Ser Gly Ala Ala Ala Gly Met Ala Leu Arg Tyr Glu Ala Phe Gln
    515                 520                 525

Gln Gly His Cys Tyr Glu Pro Phe Val Lys Tyr Gly Asn Phe Ser Ser
    530                 535                 540

Ser Thr Pro Thr Tyr Pro Val Gly Thr Thr Val Glu Phe Ser Cys Asp
545                 550                 555                 560

Pro Gly Tyr Thr Leu Glu Gln Gly Ser Ile Ile Ile Glu Cys Val Asp
                565                 570                 575

Pro His Asp Pro Gln Trp Asn Glu Thr Glu Pro Ala Cys Arg Ala Val
            580                 585                 590

Cys Ser Gly Glu Ile Thr Asp Ser Ala Gly Val Val Leu Ser Pro Asn
    595                 600                 605

Trp Pro Glu Pro Tyr Gly Arg Gly Gln Asp Cys Ile Trp Gly Val His
    610                 615                 620

Val Glu Glu Asp Lys Arg Ile Met Leu Asp Ile Arg Val Leu Arg Ile
625                 630                 635                 640

Gly Pro Gly Asp Val Leu Thr Phe Tyr Asp Gly Asp Asp Leu Thr Ala
                645                 650                 655

Arg Val Leu Gly Gln Tyr Ser Gly Pro Arg Ser His Phe Lys Leu Phe
            660                 665                 670

Thr Ser Met Ala Asp Val Thr Ile Gln Phe Gln Ser Asp Pro Gly Thr
            675                 680                 685

Ser Val Leu Gly Tyr Gln Gln Gly Phe Val Ile His Phe Glu Val
    690                 695                 700

Pro Arg Asn Asp Thr Cys Pro Glu Leu Pro Glu Ile Pro Asn Gly Trp
705                 710                 715                 720

Lys Ser Pro Ser Gln Pro Glu Leu Val His Gly Thr Val Thr Tyr
                725                 730                 735

Gln Cys Tyr Pro Gly Tyr Gln Val Val Gly Ser Ser Val Leu Met Cys
            740                 745                 750

Gln Trp Asp Leu Thr Trp Ser Glu Asp Leu Pro Ser Cys Gln Arg Val
            755                 760                 765
```

Thr Ser Cys His Asp Pro Gly Asp Val Glu His Ser Arg Arg Leu Ile
    770                 775                 780

Ser Ser Pro Lys Phe Pro Val Gly Ala Thr Val Gln Tyr Ile Cys Asp
785                 790                 795                 800

Gln Gly Phe Val Leu Met Gly Ser Ser Ile Leu Thr Cys His Asp Arg
                805                 810                 815

Gln Ala Gly Ser Pro Lys Trp Ser Asp Arg Ala Pro Lys Cys Leu Leu
            820                 825                 830

Glu Gln Leu Lys Pro Cys His Gly Leu Ser Ala Pro Glu Asn Gly Ala
        835                 840                 845

Arg Ser Pro Glu Lys Gln Leu His Pro Ala Gly Ala Thr Ile His Phe
    850                 855                 860

Ser Cys Ala Pro Gly Tyr Val Leu Lys Gly Gln Ala Ser Ile Lys Cys
865                 870                 875                 880

Val Pro Gly His Pro Ser His Trp Ser Asp Pro Pro Ile Cys Arg
                885                 890                 895

Ala Ala Ser Leu Asp Gly Phe Tyr Asn Ser Arg Ser Leu Asp Val Ala
                900                 905                 910

Lys Ala Pro Ala Ala Ser Ser Thr Leu Asp Ala Ala His Ile Ala Ala
            915                 920                 925

Ala Ile Phe Leu Pro Leu Val Ala Met Val Leu Leu Val Gly Gly Val
        930                 935                 940

Tyr Phe Tyr Phe Ser Arg Leu Gln Gly Lys Ser Ser Leu Gln Leu Pro
945                 950                 955                 960

Arg Pro Arg Pro Arg Pro Tyr Asn Arg Ile Thr Ile Glu Ser Ala Phe
                965                 970                 975

Asp Asn Pro Thr Tyr Glu Thr Gly Ser Leu Ser Phe Ala Gly Asp Glu
            980                 985                 990

Arg Ile

<210> SEQ ID NO 2
<211> LENGTH: 993
<212> TYPE: PRT
<213> ORGANISM: Homo sapiens

<400> SEQUENCE: 2

Met Arg Pro Val Ala Leu Leu Leu Pro Ser Leu Leu Ala Leu Leu
1               5                   10                  15

Ala His Gly Leu Ser Leu Glu Ala Pro Thr Val Gly Lys Gly Gln Ala
            20                  25                  30

Pro Gly Ile Glu Glu Thr Asp Gly Glu Leu Thr Ala Ala Pro Thr Pro
        35                  40                  45

Glu Gln Pro Glu Arg Gly Val His Phe Val Thr Thr Ala Pro Thr Leu
    50                  55                  60

Lys Leu Leu Asn His His Pro Leu Leu Glu Glu Phe Leu Gln Glu Gly
65                  70                  75                  80

Leu Glu Lys Gly Asp Glu Glu Leu Arg Pro Ala Leu Pro Phe Gln Pro
                85                  90                  95

Asp Pro Pro Ala Pro Phe Thr Pro Ser Pro Leu Pro Arg Leu Ala Asn
            100                 105                 110

Gln Asp Ser Arg Pro Val Phe Thr Ser Pro Thr Pro Ala Met Ala Ala
        115                 120                 125

Val Pro Thr Gln Pro Gln Ser Lys Glu Gly Pro Trp Ser Pro Glu Ser
    130                 135                 140

```
Glu Ser Pro Met Leu Arg Ile Thr Ala Pro Leu Pro Pro Gly Pro Ser
145                 150                 155                 160

Met Ala Val Pro Thr Leu Gly Pro Gly Glu Ile Ala Ser Thr Thr Pro
                165                 170                 175

Pro Ser Arg Ala Trp Thr Pro Thr Gln Glu Gly Pro Gly Asp Met Gly
            180                 185                 190

Arg Pro Trp Val Ala Glu Val Val Ser Gln Gly Ala Gly Ile Gly Ile
        195                 200                 205

Gln Gly Thr Ile Thr Ser Ser Thr Ala Ser Gly Asp Asp Glu Glu Thr
    210                 215                 220

Thr Thr Thr Thr Thr Ile Ile Thr Thr Thr Ile Thr Thr Val Gln Thr
225                 230                 235                 240

Pro Gly Pro Cys Ser Trp Asn Phe Ser Gly Pro Glu Gly Ser Leu Asp
                245                 250                 255

Ser Pro Thr Asp Leu Ser Ser Pro Thr Asp Val Gly Leu Asp Cys Phe
                260                 265                 270

Phe Tyr Ile Ser Val Tyr Pro Gly Tyr Gly Val Glu Ile Lys Val Gln
            275                 280                 285

Asn Ile Ser Leu Arg Glu Gly Glu Thr Val Thr Val Glu Gly Leu Gly
    290                 295                 300

Gly Pro Asp Pro Leu Pro Leu Ala Asn Gln Ser Phe Leu Leu Arg Gly
305                 310                 315                 320

Gln Val Ile Arg Ser Pro Thr His Gln Ala Ala Leu Arg Phe Gln Ser
                325                 330                 335

Leu Pro Pro Pro Ala Gly Pro Gly Thr Phe His Phe His Tyr Gln Ala
                340                 345                 350

Tyr Leu Leu Ser Cys His Phe Pro Arg Arg Pro Ala Tyr Gly Asp Val
            355                 360                 365

Thr Val Thr Ser Leu His Pro Gly Gly Ser Ala Arg Phe His Cys Ala
        370                 375                 380

Thr Gly Tyr Gln Leu Lys Gly Ala Arg His Leu Thr Cys Leu Asn Ala
385                 390                 395                 400

Thr Gln Pro Phe Trp Asp Ser Lys Glu Pro Val Cys Ile Ala Ala Cys
                405                 410                 415

Gly Gly Val Ile Arg Asn Ala Thr Thr Gly Arg Ile Val Ser Pro Gly
                420                 425                 430

Phe Pro Gly Asn Tyr Ser Asn Asn Leu Thr Cys His Trp Leu Leu Glu
            435                 440                 445

Ala Pro Glu Gly Gln Arg Leu His Leu His Phe Glu Lys Val Ser Leu
        450                 455                 460

Ala Glu Asp Asp Asp Arg Leu Ile Ile Arg Asn Gly Asp Asn Val Glu
465                 470                 475                 480

Ala Pro Pro Val Tyr Asp Ser Tyr Glu Val Glu Tyr Leu Pro Ile Glu
                485                 490                 495

Gly Leu Leu Ser Ser Gly Lys His Phe Phe Val Glu Leu Ser Thr Asp
            500                 505                 510

Ser Ser Gly Ala Ala Ala Gly Met Ala Leu Arg Tyr Glu Ala Phe Gln
        515                 520                 525

Gln Gly His Cys Tyr Glu Pro Phe Val Lys Tyr Gly Asn Phe Ser Ser
    530                 535                 540

Ser Thr Pro Thr Tyr Pro Val Gly Thr Thr Val Glu Phe Ser Cys Asp
545                 550                 555                 560

Pro Gly Tyr Thr Leu Glu Gln Gly Ser Ile Ile Ile Glu Cys Val Asp
```

```
                565                 570                 575
Pro His Asp Pro Gln Trp Asn Glu Thr Glu Pro Ala Cys Arg Ala Val
            580                 585                 590
Cys Ser Gly Glu Ile Thr Asp Ser Ala Gly Val Val Leu Ser Pro Asn
            595                 600                 605
Trp Pro Glu Pro Tyr Gly Arg Gly Gln Asp Cys Ile Trp Gly Val His
            610                 615                 620
Val Glu Glu Asp Lys Arg Ile Met Leu Asp Ile Arg Val Leu Arg Ile
625                 630                 635                 640
Gly Pro Gly Asp Val Leu Thr Phe Tyr Asp Gly Asp Leu Thr Ala
                645                 650                 655
Arg Val Leu Gly Gln Tyr Ser Gly Pro Arg Ser His Phe Lys Leu Phe
            660                 665                 670
Thr Ser Met Ala Asp Val Thr Ile Gln Phe Gln Ser Asp Pro Gly Thr
            675                 680                 685
Ser Val Leu Gly Tyr Gln Gln Gly Phe Val Ile His Phe Phe Glu Val
            690                 695                 700
Pro Arg Asn Asp Thr Cys Pro Glu Leu Pro Glu Ile Pro Asn Gly Trp
705                 710                 715                 720
Lys Ser Pro Ser Gln Pro Glu Leu Val His Gly Thr Val Val Thr Tyr
                725                 730                 735
Gln Cys Tyr Pro Gly Tyr Gln Val Val Gly Ser Ser Val Leu Met Cys
            740                 745                 750
Gln Trp Asp Leu Thr Trp Ser Glu Asp Leu Pro Ser Cys Gln Arg Val
            755                 760                 765
Thr Ser Cys His Asp Pro Gly Asp Val Glu His Ser Arg Arg Leu Ile
            770                 775                 780
Ser Ser Pro Lys Phe Pro Val Gly Ala Thr Val Gln Tyr Ile Cys Asp
785                 790                 795                 800
Gln Gly Phe Val Leu Met Gly Ser Ser Ile Leu Thr Cys His Asp Arg
                805                 810                 815
Gln Ala Gly Ser Pro Lys Trp Ser Asp Arg Ala Pro Lys Cys Leu Leu
            820                 825                 830
Glu Gln Leu Lys Pro Cys His Gly Leu Ser Ala Pro Glu Asn Gly Ala
            835                 840                 845
Arg Ser Pro Glu Lys Gln Leu His Pro Gly Ala Thr Ile His Phe
850                 855                 860
Ser Cys Ala Pro Gly Tyr Val Leu Lys Gly Gln Ala Ser Ile Lys Cys
865                 870                 875                 880
Val Pro Gly His Pro Ser His Trp Ser Asp Pro Pro Ile Cys Arg
                885                 890                 895
Ala Ala Ser Leu Asp Gly Phe Tyr Asn Ser Arg Ser Leu Asp Val Ala
            900                 905                 910
Lys Ala Pro Ala Ala Ser Ser Thr Leu Asp Ala Ala His Ile Ala Ala
            915                 920                 925
Ala Ile Phe Leu Pro Leu Val Ala Met Val Leu Leu Val Gly Gly Val
            930                 935                 940
Tyr Phe Tyr Phe Ser Arg Leu Gln Gly Lys Ser Ser Leu Gln Leu Pro
945                 950                 955                 960
Arg Pro Arg Pro Arg Pro Tyr Asn Arg Ile Thr Ile Glu Ser Ala Phe
                965                 970                 975
Asp Asn Pro Thr Tyr Glu Thr Gly Glu Thr Arg Glu Tyr Glu Val Ser
            980                 985                 990
```

Ile

<210> SEQ ID NO 3
<211> LENGTH: 444
<212> TYPE: PRT
<213> ORGANISM: Artificial Sequence
<220> FEATURE:
<223> OTHER INFORMATION: Synthetic polypeptide

<400> SEQUENCE: 3

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Ser
            20                  25                  30

Trp Ile Asn Trp Val Arg Gln Met Pro Gly Lys Gly Leu Glu Trp Met
        35                  40                  45

Gly Arg Ile Tyr Pro Gly Glu Gly Asp Thr Asn Tyr Asn Gly Asn Phe
    50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gly Leu Val Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Ser Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
            435                 440

<210> SEQ ID NO 4
<211> LENGTH: 218
<212> TYPE: PRT
<213> ORGANISM: Artificial Sequence
<220> FEATURE:
<223> OTHER INFORMATION: Synthetic polypeptide

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Tyr Asn
            20                  25                  30

Gly Ile Ser Tyr Met His Trp Tyr Gln Gln Lys Pro Gly Gln Ala Pro
        35                  40                  45

Arg Leu Leu Ile Tyr Ala Ala Ser Asn Val Gln Ser Gly Ile Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Ile
                85                  90                  95

Glu Asp Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 5
<211> LENGTH: 1938
<212> TYPE: DNA
<213> ORGANISM: Artificial Sequence
<220> FEATURE:
<223> OTHER INFORMATION: Synthetic polynucleotide

<400> SEQUENCE: 5

```
gaagtccaac tcgtccaatc cggtgccgaa gtgaaaaagc ctggggaatc cctgaagatc      60
agctgcaagg gatccggtta ctcgttcacc tcctcctgga ttaactgggt ccggcagatg     120
cccggaaagg gactggagtg gatgggcaga atctatccgg gcgaagggga cactaattac     180
aacggaaact tcgagggcca ggtcaccatt tcggccgata gagcatctc aaccgcgtac     240 ttgcagtggt caagcctgaa ggcttccgac accgccatgt actactgtac tcgcggcctt     300
gtgatggact actggggaca gggaactctc gtgaccgtgt cgtccgcctc taccaagggc     360
ccttccgtgt tccctctggc cccctcgagc aagagcacct ctgggggcac agcggccctg     420
ggctgcctgg tcaaggacta cttccccgag ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg gtgagaggcc agcacaggga     660
gggagggtgt ctgctggaag ccaggctcag cgctcctgcc tggacgcatc ccggctatgc     720
agccccagtc cagggcagca aggcaggccc cgtctgcctc ttcacccgga ggcctctgcc     780
cgccccactc atgctcaggg agagggtctt ctggcttttt ccccaggctc tgggcaggca     840
caggctaggt gcccctaacc caggccctgc acacaaaggg gcaggtgctg ggctcagacc     900
tgccaagagc catatccggg aggaccctgc ccctgaccta agcccacccc aaaggccaaa     960
ctctccactc cctcagctcg gacaccttct ctcctcccag attccagtaa ctcccaatct    1020
tctctctgca gagcccaaat ctagtgacaa aactcacaca tgcccaccgt gcccaggtaa    1080
gccagcccag gcctcgccct ccagctcaag cgggacagg tgccctagag tagcctgcat    1140
ccagggacag gccccagccg ggtgctgaca cgtccacctc catctcttcc tcagcacctg    1200
aactcctggg gggaccgtca gtcttcctct tccccccaaa acccaaggac accctcatga    1260
tctcccggac ccctgaggtc acatgcgtgg tggtggacgt gagccacgaa gaccctgagg    1320
tcaagttcaa ctggtacgtg gacggcgtgg aggtgcataa tgccaagaca aagccgcggg    1380
aggagcagta caacagcacg taccgtgtgg tcagcgtcct caccgtcctg caccaggact    1440
ggctgaatgg caaggagtac aagtgcaagg tctccaacaa agcccctccca gcccccatcg    1500 agaaaaccat ctccaaagcc aaaggtggga cccgtggggt gcgagggcca catggacaga    1560
ggccggctcg gcccaccctc tgccctgaga gtgaccgctg taccaacctc tgtccctaca    1620
gggcagcccc gagaaccaca ggtgtacacc ctgcccccat cccgggatga gctgaccaag    1680
aaccaggtca gcctgacctg cctggtcaaa ggcttctatc ccagcgacat cgccgtggag    1740
tgggagagca atgggcagcc ggagaacaac tacaagacca cgcctcccgt gctggactcc    1800
gacggctcct tcttcctcta cagcaagctc accgtggaca agagcaggtg gcagcagggg    1860
aacgtcttct catgctccgt gatgcatgag gctctgcaca accactacac gcagaagagc    1920
ctctccctgt ctccgggt                                                  1938
```

<210> SEQ ID NO 6
<211> LENGTH: 654
<212> TYPE: DNA
<213> ORGANISM: Artificial Sequence
<220> FEATURE:
<223> OTHER INFORMATION: Synthetic polynucleotide

<400> SEQUENCE: 6

```
gaaatcgtgt tgacccagtc ccccgctacc ctgtcactga gccccggaga acgcgcgact      60
```

| | | |
|---|---|---|
| ctgtcctgcc gggcatccca gtccgtggac tacaacggaa tctcctacat gcactggtat | 120 |
| cagcaaaagc caggccaagc cccgagactg ctcatctacg ccgcctcgaa cgtgcagagc | 180 |
| ggtattccgg cgcggttctc cggctcgggc agcggaaccg attttaccct cactatctcg | 240 |
| tcacttgaac ctgaggactt cgccgtgtac tactgccagc agtccattga ggacccgcct | 300 |
| actttcgggg ggggaaccaa agtcgagatc aagcggactg tggctgcacc aagtgtcttc | 360 |
| atcttcccgc catctgatga gcagttgaaa tctggaactg cctctgttgt gtgcctgctg | 420 |
| aataacttct atcccagaga ggccaaagta cagtggaagg tggataacgc cctccaatcg | 480 |
| ggtaactccc aggagagtgt cacagagcag gacagcaagg acagcaccta cagcctcagc | 540 |
| agcaccctga cgctgagcaa agcagactac gagaaacaca agtctacgc ctgcgaagtc | 600 |
| acccatcagg gcctgagctc gcccgtcaca aagagcttca caggggaga gtgt | 654 |

```
<210> SEQ ID NO 7
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Ser
                20                  25                  30

Trp Ile Asn Trp Val Arg Gln Met Pro Gly Lys Gly Leu Glu Trp Met
            35                  40                  45

Gly Arg Ile Tyr Pro Gly Glu Gly Asp Thr Asn Tyr Asn Gly Asn Phe
        50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gly Leu Val Met Asp Tyr Trp Gly Gln Gly Thr Leu Val Thr
            100                 105                 110

Val Ser Ser
        115

<210> SEQ ID NO 8
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Tyr Asn
                20                  25                  30

Gly Ile Ser Tyr Met His Trp Tyr Gln Gln Lys Pro Gly Gln Ala Pro
            35                  40                  45

Arg Leu Leu Ile Tyr Ala Ala Ser Asn Val Gln Ser Gly Ile Pro Ala
        50                  55                  60

Arg Phe Ser Gly Ser Gly Ser Gly Thr Asp Phe Thr Leu Thr Ile Ser
65                  70                  75                  80
```

```
Ser Leu Glu Pro Glu Asp Phe Ala Val Tyr Tyr Cys Gln Gln Ser Ile
                85                  90                  95

Glu Asp Pro Pro Thr Phe Gly Gly Gly Thr Lys Val Glu Ile Lys
            100                 105                 110
```